United States Patent
Kalarn et al.

(10) Patent No.: US 11,483,537 B2
(45) Date of Patent: Oct. 25, 2022

(54) STEREOSCOPIC MOBILE RETINAL IMAGER

(71) Applicant: Spect Inc., Palo Alto, CA (US)

(72) Inventors: Sachin Kalarn, Baltimore, MD (US);
Ankur Sudhir Gupta, Plano, TX (US)

(73) Assignee: Spect Inc., Palo Alto, CA (US)

( * ) Notice: Subject to any disclaimer, the term of this patent is extended or adjusted under 35 U.S.C. 154(b) by 527 days.

(21) Appl. No.: 16/681,273

(22) Filed: Nov. 12, 2019

(65) Prior Publication Data

US 2020/0084430 A1 Mar. 12, 2020

Related U.S. Application Data

(63) Continuation of application No. PCT/US2018/033029, filed on May 16, 2018.
(Continued)

(51) Int. Cl.
*H04N 13/239* (2018.01)
*A61B 3/00* (2006.01)
(Continued)

(52) U.S. Cl.
CPC ......... *H04N 13/239* (2018.05); *A61B 3/0008* (2013.01); *A61B 3/1208* (2013.01);
(Continued)

(58) Field of Classification Search
CPC .. H04N 13/239; H04N 5/2254; H04N 5/2256; H04N 5/2252; H04N 13/10;
(Continued)

(56) References Cited

U.S. PATENT DOCUMENTS

| | | | |
|---|---|---|---|
| 5,008,865 A | | 4/1991 | Shaffer et al. |
| 5,504,542 A | * | 4/1996 | Hino ...................... A61B 3/132 351/208 |

(Continued)

FOREIGN PATENT DOCUMENTS

| | | |
|---|---|---|
| EP | 0717569 A2 * | 12/1995 |
| WO | WO-2015/054672 A1 | 4/2015 |
| WO | WO-2017/180965 A1 | 10/2017 |

OTHER PUBLICATIONS

Advanced Photonix, Inc. (2006). CdS Photoconductive photocells—PDV-P8001, 1 total page.
(Continued)

*Primary Examiner* — Albert H Cutler
(74) *Attorney, Agent, or Firm* — Cooley LLP

(57) ABSTRACT

Disclosed herein are devices and methods for generating stereoscopic views of the eye (or any desired anatomic structure) using a dual-camera portable computing device. The locations of the two cameras are fixed, and the camera lenses may have different focal lengths. For example, the focal length of the second camera lens may be longer than the focal length of the first camera lens. One variation of a detachable imaging system comprises an objective lens and a relay lens that are disposed over the two cameras. The relay lens may be disposed over the first and second cameras, and have a focal length that is greater than the focal length of the first camera lens and less than or equal to the focal length of the second camera lens.

33 Claims, 19 Drawing Sheets

Related U.S. Application Data

(60) Provisional application No. 62/603,029, filed on May 16, 2017.

(51) Int. Cl.
| | |
|---|---|
| *A61B 3/12* | (2006.01) |
| *A61B 3/14* | (2006.01) |
| *H04N 5/225* | (2006.01) |
| *G06V 40/19* | (2022.01) |
| *H04N 13/10* | (2018.01) |
| *H04N 13/204* | (2018.01) |
| *H04N 13/207* | (2018.01) |
| *H04N 13/236* | (2018.01) |
| *H04N 13/25* | (2018.01) |

(52) U.S. Cl.
CPC .......... *A61B 3/145* (2013.01); *H04N 5/2254* (2013.01); *H04N 5/2256* (2013.01); *G06V 40/19* (2022.01)

(58) Field of Classification Search
CPC .. H04N 13/204; H04N 13/207; H04N 13/236; H04N 13/25; A61B 3/0008; A61B 3/1208; A61B 3/145; A61B 3/00; A61B 3/10; A61B 3/1216; A61B 3/14; G06V 40/19
See application file for complete search history.

(56) References Cited

U.S. PATENT DOCUMENTS

| | | | |
|---|---|---|---|
| 5,543,816 | A | 8/1996 | Heacock |
| 7,048,379 | B2 | 5/2006 | Miller et al. |
| 7,499,588 | B2 | 3/2009 | Jacobs et al. |
| 7,561,191 | B2 | 7/2009 | May et al. |
| 8,743,194 | B2 | 6/2014 | Fletcher et al. |
| 8,789,695 | B2 | 7/2014 | Mason |
| 9,154,594 | B2 | 10/2015 | Fletcher et al. |
| 9,325,884 | B2 | 4/2016 | Fletcher et al. |
| 9,357,920 | B2 | 6/2016 | Yates et al. |
| 9,398,851 | B2 | 7/2016 | Anand et al. |
| 9,523,845 | B2 | 12/2016 | Fletcher et al. |
| 10,105,051 | B2 | 10/2018 | Gupta |
| 11,129,532 | B2 * | 9/2021 | Fletcher .................. A61B 3/12 |
| 2003/0208125 | A1 | 11/2003 | Watkins |
| 2007/0280677 | A1 | 12/2007 | Drake et al. |
| 2008/0278686 | A1 | 11/2008 | Kasper et al. |
| 2012/0287255 | A1 | 11/2012 | Ignatovich et al. |
| 2013/0028591 | A1 | 1/2013 | Hicks |
| 2013/0083185 | A1 | 4/2013 | Coleman, III |
| 2013/0128223 | A1 | 5/2013 | Wood et al. |
| 2014/0055736 | A1 | 2/2014 | Ishak |
| 2014/0285766 | A1 | 9/2014 | Kohn Bitran |
| 2015/0097924 | A1 | 4/2015 | Hauk |
| 2016/0007008 | A1 | 1/2016 | Molgaard et al. |
| 2016/0066783 | A1 | 3/2016 | Kislinger et al. |
| 2016/0205298 | A1 * | 7/2016 | Zhou .................. A61B 3/1015 348/78 |
| 2016/0296111 | A1 | 10/2016 | Russo |
| 2016/0296112 | A1 | 10/2016 | Fletcher et al. |
| 2017/0055831 | A1 | 3/2017 | Miwa et al. |
| 2017/0119250 | A1 * | 5/2017 | Kolachalama ....... A61B 5/0022 |
| 2017/0126943 | A1 | 5/2017 | Fletcher et al. |
| 2017/0160533 | A1 | 6/2017 | Fletcher et al. |
| 2017/0161892 | A1 | 6/2017 | Tellatin et al. |
| 2019/0090740 | A1 | 3/2019 | Gupta |
| 2020/0084430 | A1 | 3/2020 | Kalarn et al. |

OTHER PUBLICATIONS

D-Eye smartphone-based retinal imaging system (2018), 7 total pages.

Guangzhou MeCan Medical (2017). High definition ophthalmic equipment non mydriatic portable digital fundus camera, 4 total pages.

Haddock, L.J. et al. (2013). "Simple, inexpensive technique for high-quality smartphone fundus photography in human and animal eyes," 2013, 5 total pages.

Haddock, L.J. et al. (2016). "Teleophthalmology of retinal diseases—Updates on telemedicine for diabetic retinopathy screening and smartphone funduscopy," *Retinal Physician* 8 total pages.

International Search Report dated Jul. 13, 2018, for PCT Application No. PCT/US2018/029886, filed on Apr. 27, 2018, 4 pages.

International Search Report dated Aug. 3, 2018, for PCT Application No. PCT/US2018/033029, filed on May 16, 2018, 2 pages.

Jain, D. et al. (2016). "Open-source, ultra-low cost smartphone attachment for non-mydriatic fundus photography—Open indirect ophthalmoscope," ARVO Annual Meeting Abstract, Sep. 2016, 3 total pages.

Jin, K. et al. (2017). "Telemedicine screening of retinal diseases with a handheld portable non-mydriatic fundus camera," *BMC Ophthalm.* 2017, 7 total pages.

Miller, M. (2016). "Smartphone Dual Camera Showdown: Two Cameras, different focus," located at https://www.zdnet.com/article/smartphone-dual-camera-showdown-two-cameras-different-focus/, 7 total pages.

Non-Final Office Action dated Jan. 25, 2017, for U.S. Appl. No. 15/076,824, filed Mar. 22, 2016, 9 pages.

Non-Final Office Action dated Jul. 17, 2019, for U.S. Appl. No. 16/152,294, filed Oct. 4, 2018, 13 pages.

Notice of Allowance dated Jun. 14, 2018, for U.S. Appl. No. 15/076,824, filed Mar. 22, 2016, 8 pages.

Notice of Allowance dated Sep. 24, 2018, for U.S. Appl. No. 15/076,824, filed Mar. 22, 2016, 5 pages.

Notice of Allowance dated Jan. 27, 2020, for U.S. Appl. No. 16/152,294, filed Oct. 4, 2018, 8 pages.

Notice of Allowance dated May 5, 2020, for U.S. Appl. No. 16/152,294, filed Oct. 4, 2018, 8 pages.

Peek Eye Care (2018). Peek Eye Care Overview, 6 total pages.

Russo, A. et al. (2015). "A novel device to exploit the smartphone camera for fundus photography," *J. Ophthalm.* 2015, 5 total pages.

Ryan, M.E. et al. (2015). "Comparison Among Methods of Retinopathy Assessment (CAMRA) Study: Smartphone, Nonmydriatic, and Mydriatic Photography," *Ophthalm.* 122:2038-2043.

Shen, B.Y. et al. (2017). "A portable, inexpensive, nonmydriatic fundus camera based on the Raspberry Pi® Computer," *J. Ophthalm.* 2017, 5 total pages.

Smartphone Ophthalmoscope and smartphone retinal camera (2018), 11 total pages.

Volk iNview (2016). iPhone Fundus Camera, Product Description, located at https://volk.com/index.php/inview.html, 3 total pages.

Volk iNview User's Manual/Instructions for Use (2016). Retinal Camera, 35 total pages.

Written Opinion of the International Searching Authority dated Jul. 13, 2018, for PCT Application No. PCT/US2018/029886, filed on Apr. 27, 2018, 10 pages.

Written Opinion of the International Searching Authority dated Aug. 3, 2018, for PCT Application No. PCT/US2018/033029, filed on May 16, 2018, 4 pages.

\* cited by examiner

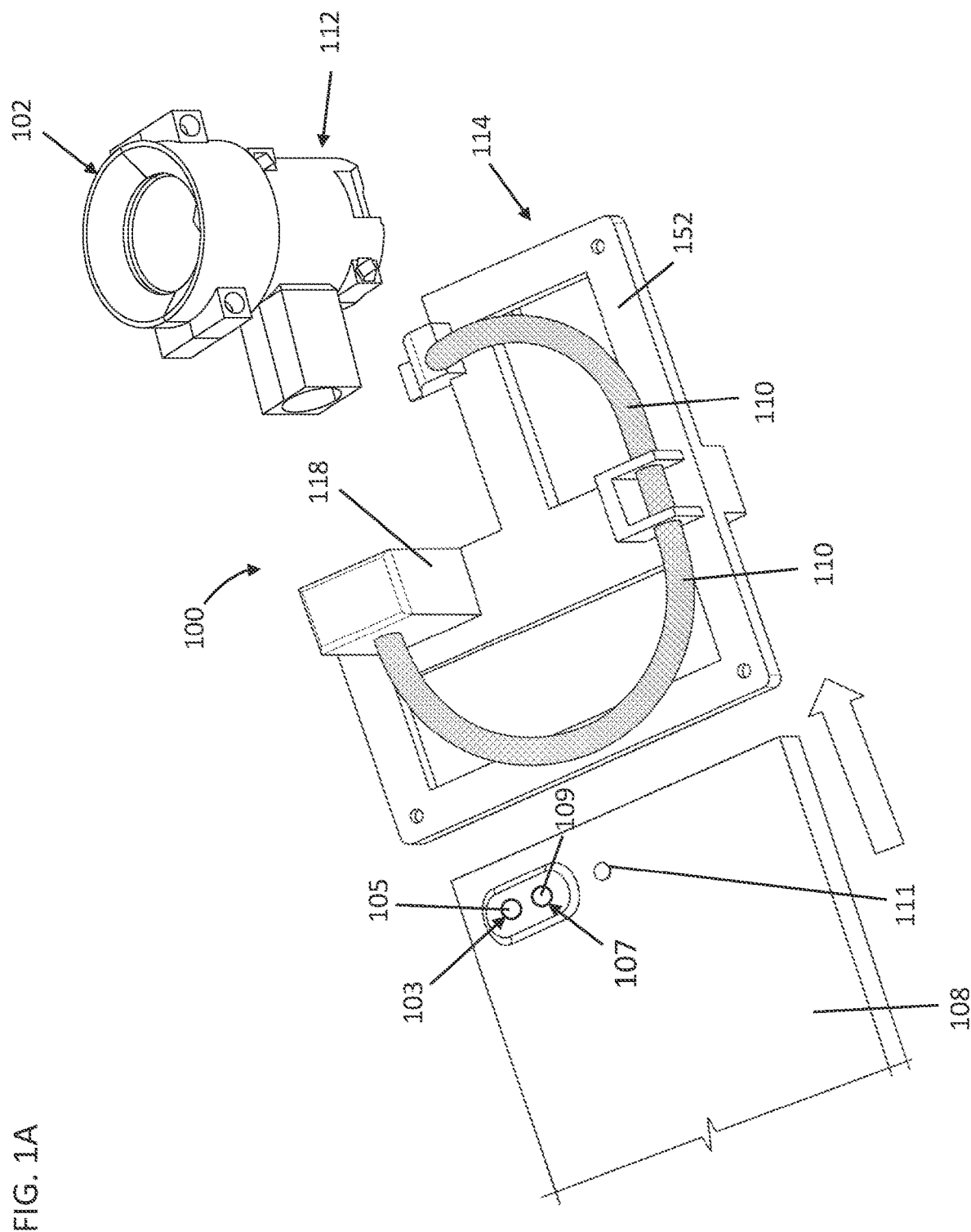

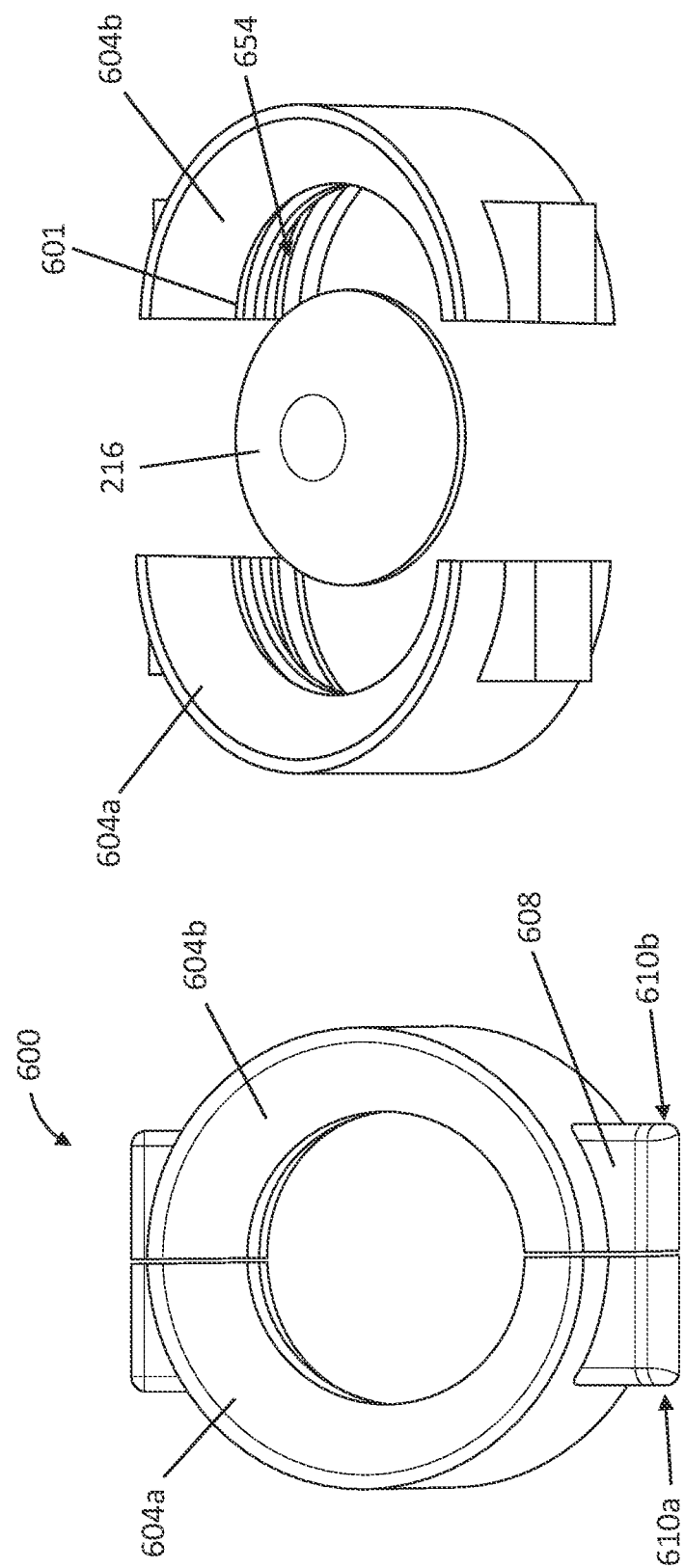

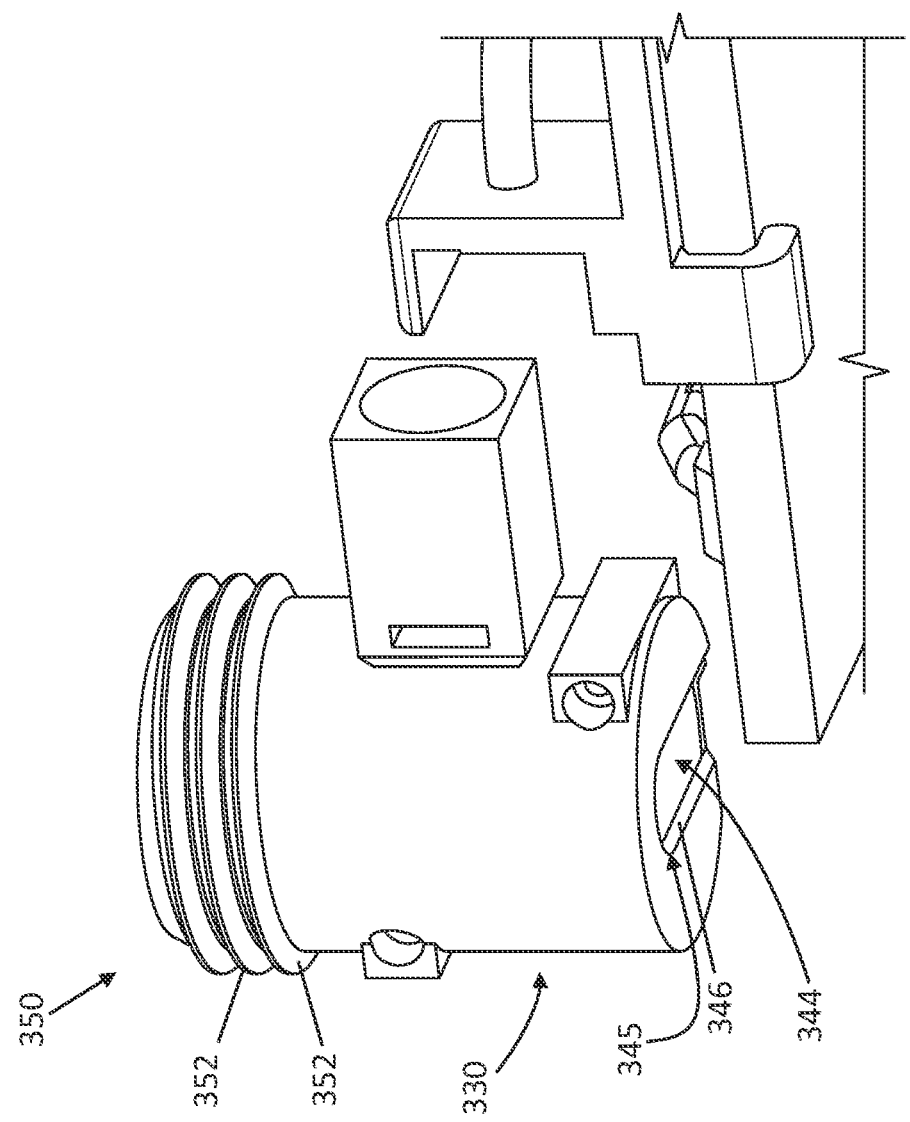

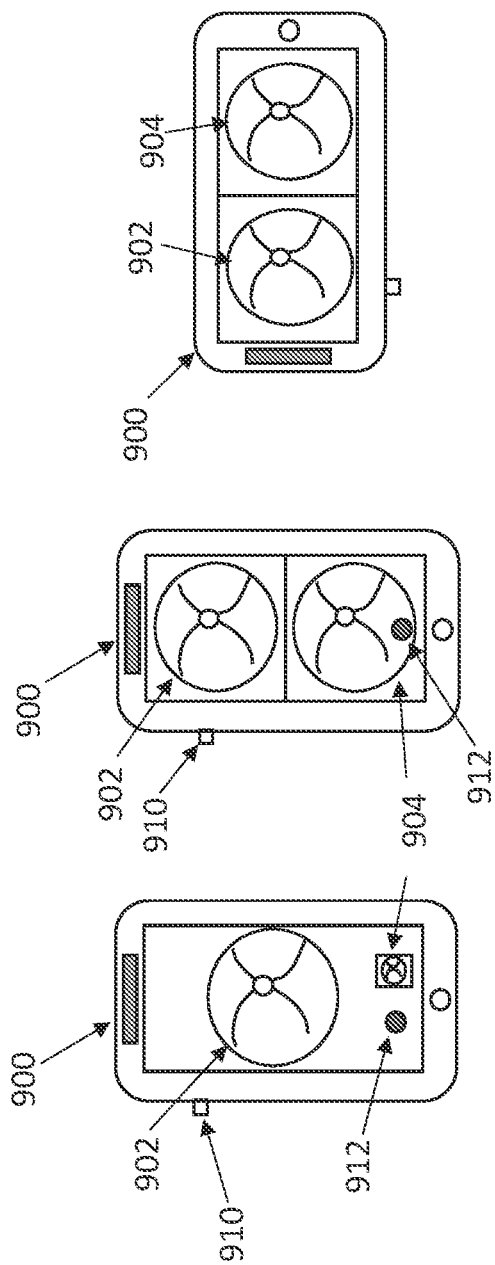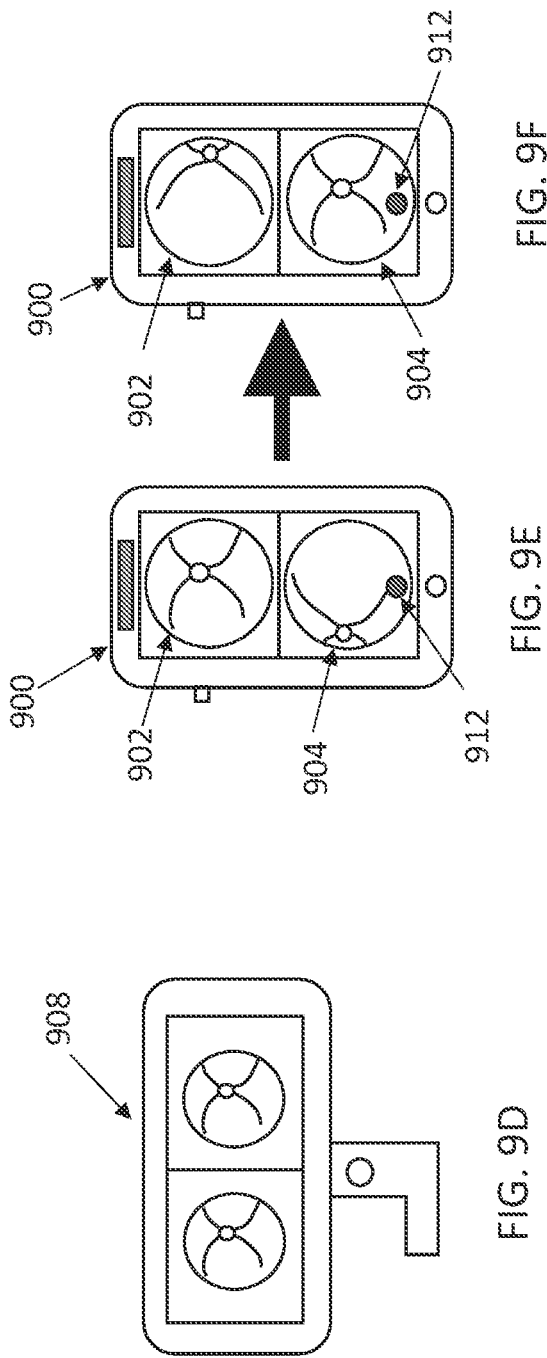

STEREOSCOPIC MOBILE RETINAL IMAGER

CROSS-REFERENCE TO RELATED APPLICATIONS

This application is a continuation application of International Application No. PCT/US2018/033029, filed May 16, 2018, which claims priority to U.S. Patent Application No. 62/603,029, filed May 16, 2017, the disclosures of which are hereby incorporated by reference in their entirety.

BACKGROUND

Regular and accessible eye screening can help promote early detection of ophthalmic diseases such as diabetic retinopathy and glaucoma, and help prevent those diseases from progressing further and leading to blindness. Furthermore, some diseases such as glaucoma involve a thorough examination and assessment of the optic nerve head in order to identify any pathologies. While 3-D or stereoscopic imaging or viewing of the eye may facilitate the assessment of various structure of the eye, the availability of such specialized equipment is typically limited to ophthalmologists' offices. Access to physicians who have specialized equipment for eye screening and expertise in diagnosing ophthalmic diseases may be a major challenge for individuals who live in rural areas and/or regions where there are few (if any) eye care specialists. This may lead to delays in medical care for preventable and irreversible causes of blindness.

Accordingly, it is desirable to develop simple, inexpensive, and portable eye screening equipment that can acquire stereoscopic or 3-D images of the retina and/or fundus region of the eye.

SUMMARY

Disclosed herein are devices and methods for generating stereoscopic views of the fundus (or any anatomic structure) using a dual-camera portable computing device, where the camera lenses are coplanar and/or have substantially parallel central axes. In some variations, the dual-cameras may have different focal lengths. One variation of a system for generating stereoscopic views of the fundus of an eye may comprise a portable computing device having two cameras, and a detachable imaging system comprising an optical lens assembly and a portable computing device case configured to couple to the portable computing device such that the optical lens assembly is disposed over the two cameras. The portable computing device may be a dual-camera portable computing device (e.g., a smartphone having two cameras adjacent to each other), where the locations, orientations, lenses of the cameras are fixed. In one variation, the portable computing device may comprise a first camera having a first lens with a first focal length and a second camera having a second lens with a second focal length that may be greater than or equal to the first focal length. For example, the first lens may be a wide-angle lens (e.g., a lens having a focal length of about 35 mm or wider) while the second lens may be a telephoto lens (e.g., a lens having a focal length of about 50 mm or more). The relative locations of the first and second cameras may be fixed such that the first and second lenses are coplanar and/or their central axes (i.e., an axis that is perpendicular to the plane of the lens that passes through the center of the lens) may be parallel to each other. The first and second cameras may be separated from each other by a space having a predetermined length, which may be less than about 30 mm, e.g., about 8 mm, about 10 mm, about 10.5 mm, about 12 mm, about 15 mm, etc. The optical lens assembly of the detachable imaging system may comprise an objective lens with an objective lens focal length and a relay lens with a relay lens focal length. The objective lens and the relay lens may be aligned such that their focal points are co-localized at a location or point between them, for example, at a location between the focal points of the first and second cameras. The relay lens may be sized to span across both cameras of the portable computing device. For example, the relay lens may have a diameter that is greater than or equal to the sum of the diameter of the first camera lens, the diameter of the second camera lens, and the separation distance between the first and second cameras. In some variations, relay lens focal length may be less than or equal to the difference between the second focal length and the objective lens focal length, and greater than the first focal length. The images captured by the first and second cameras through the optical lens assembly may be used to generate a stereoscopic view. In some variations, the objective lens may be detachably coupled to the optical lens assembly such that objective lenses with different optical properties (e.g., filters, focal lengths, etc.) may be used to image different aspects of the eye and/or different anatomical regions (e.g., wound regions, oral cavity, cervix, etc.).

In some variations, the images acquired by the cameras of the portable computing device may be displayed on the portable computing device, and/or may be transmitted to a remote controller and/or display for viewing and analysis. For example, stereoscopic viewing of the images may comprise using traditional stereoscopic or prismatic glasses or a stereoscope.

One variation of a detachable imaging system configured to provide stereoscopic views for a portable computing device having two cameras may comprise a portable computing device case configured to be detachably coupled to a portable computing device, and an optical lens assembly detachably coupled to the portable computing device case, where the optical lens assembly may comprise an objective lens with an objective lens focal length and a relay lens with a relay lens focal length. The portable computing device may comprise a first camera having a first lens with a first focal length and a second camera having a second lens having a second focal length longer than the first focal length. The position of the first and second cameras of the portable computing device may be fixed relative to each other and the first and second lenses may be coplanar. A diameter of the relay lens may be greater than or equal to the sum of a diameter of the first lens, a diameter of the second lens, and a separation distance between the first and second cameras. The relay lens focal length may be less than or equal to the second focal length and greater than the first focal length. For example, the relay lens focal length may be less than or equal to the difference between the second focal length and the objective lens focal length and greater than the first focal length. In some variations, a center of the objective lens and a center of the relay lens may be aligned along an imaging axis, and a distance between the objective lens and the relay lens may be a sum of the objective lens focal length and the relay lens focal length. The optical lens assembly may be configured to be disposed over the first and second cameras when the imaging device is coupled to the portable computing device.

Optionally, the portable computing device case may comprise a light emitter. In some variations, the light emitter may comprise a fiber optic cable that optically connects the optical lens assembly with a light source of the portable computing device. The light emitter may comprise a light source, for example, a light-emitting diode. In one example, the first focal length may be about 28 mm, the second focal length may be about 56 mm, the objective lens focal length may be about 18.5 mm, and the relay lens focal length may be about 30 mm. In some variations, the objective lens focal length may be about 25 mm. The objective lens may be detachably coupled to an optical lens assembly housing of the optical lens assembly and in some variations, the objective lens may be retained within an objective lens mount. The optical lens assembly housing may comprise an attachment region with a plurality of threaded protrusions, and the objective lens mount may comprise a receiving region with a plurality of threaded grooves that correspond with the threaded protrusions.

Also disclosed herein are imaging systems for generating stereoscopic views. One variation of a system may comprise a portable computing device comprising a first camera having a first lens with a first focal length, and a second camera having a second lens with a second focal length that may be greater than or equal to the first focal length, and a detachable imaging system comprising a portable computing device case configured to releasably attach to portable computing device and an optical lens assembly configured to be disposed over the first and second camera when the detachable imaging system is coupled to the portable computing device. In some variations, the optical lens assembly may be releasably attached to the portable computing device case. The optical lens assembly may have an objective lens with an objective lens focal length and a relay lens with a relay lens focal length, and the relay lens focal length may be less than or equal to the second focal length and greater than the first focal length. In some variations, the relay lens focal length may be less than or equal to the difference between the second focal length and the objective lens focal length and greater than the first focal length. The first and the second cameras of the portable computing device may be adjacent to each other such that the first and second lenses are coplanar. The portable computing device case may have a light emitter that may be mounted on the case and the light emitter may be optically connected to the optical lens assembly. In some variations, the portable computing device may comprise a light source and the light emitter may comprise a fiber optic cable. Alternatively or additionally, the light emitter may comprise a light source, for example, a light-emitting diode. In some variations, the portable computing device may be a smartphone.

In some variations, a center of the objective lens and a center of the relay lens may be aligned along an imaging axis, and a distance between the objective lens and the relay lens may be a sum of the objective lens focal length and the relay lens focal length. The imaging axis may intersect at a midpoint of a separation distance between the first and second cameras. A central axis of the first camera and a central axis of the second camera may be parallel to each other, and a separation distance between the first and second cameras may be less than or equal to about 30 mm. The separation distance and orientations of the first and second lenses of the portable computing device may be fixed. In one variation, illumination light from the optical lens assembly may have an illumination axis that is offset from the central axes of the first and second cameras. The first lens of the portable computing device may be a wide-angle lens and the second lens of the portable computing device may be a telephoto lens. For example, the first focal length may be about 28 mm, the second focal length may be about 56 mm, the objective lens focal length may be about 18.5 mm, and the relay lens focal length may be about 30 mm. In some variations, a diameter of the relay lens may be greater than or equal to the sum of a diameter of the first lens, a diameter of the second lens, and the separation distance between the first and second cameras.

Also disclosed herein are methods for generating stereoscopic views using a dual-camera portable computing device. One variation of a method may comprise simultaneously acquiring images using a detachable imaging system disposed over a first camera and a second camera of a portable imaging device, generating a first view window on a display of the portable computing device depicting images acquired by the first camera and a second view window on the display depicting images acquired by the second camera, and generating a stereoscopic view by combining the images depicted in the first view window and the second view window. The detachable imaging system may comprise an objective lens with an objective lens focal length and a relay lens with a relay lens focal length and the relay lens may be aligned with the objective lens along an imaging axis. A diameter of the relay lens may be greater than or equal to the sum of a diameter of the first lens, a diameter of the second lens, and a separation distance between the first and second cameras. A first camera of a portable computing device may have a first lens with a first focal length and a second camera of the portable computing device may have a second lens with a second focal length that is longer than the first focal length, and the relay lens focal length may be less than or equal to the second focal length and greater than the first focal length. For example, the relay lens focal length may be less than or equal to the difference between the second focal length and the objective lens focal length and greater than the first focal length. Combining the images may comprise viewing the images in the first view window and the second view window using a pair of prismatic or stereoscopic glasses or a stereoscope. Alternatively or additionally, combining the images may comprise overlaying the images from the first camera and the second camera.

BRIEF DESCRIPTION OF THE DRAWINGS

FIG. 1A is a perspective view of one variation of a system for acquiring images for generating stereoscopic views of the eye.

FIG. 6A is a front view of one variation of an objective lens and objective lens mount.

FIG. 6B is a perspective front view of the objective lens and objective lens mount of FIG. 6A.

FIG. 7B is a perspective right-side view of an optical lens assembly and a portion of a portable computing device case.

FIGS. 9A-9C are schematic representations of various graphical user interfaces for a portable computing device application for viewing images acquired for generating stereoscopic views of the eye. FIG. 9D is a schematic representation of one variation of a graphical user interface for a remote controller or server for viewing images acquired by a portable computing device. FIGS. 9E-9F are schematic representations of a method for sequentially acquiring different views of an eye (e.g., fundus or retina of an eye that has not been fully dilated) by the systems described herein.

DETAILED DESCRIPTION

Figure 1B:
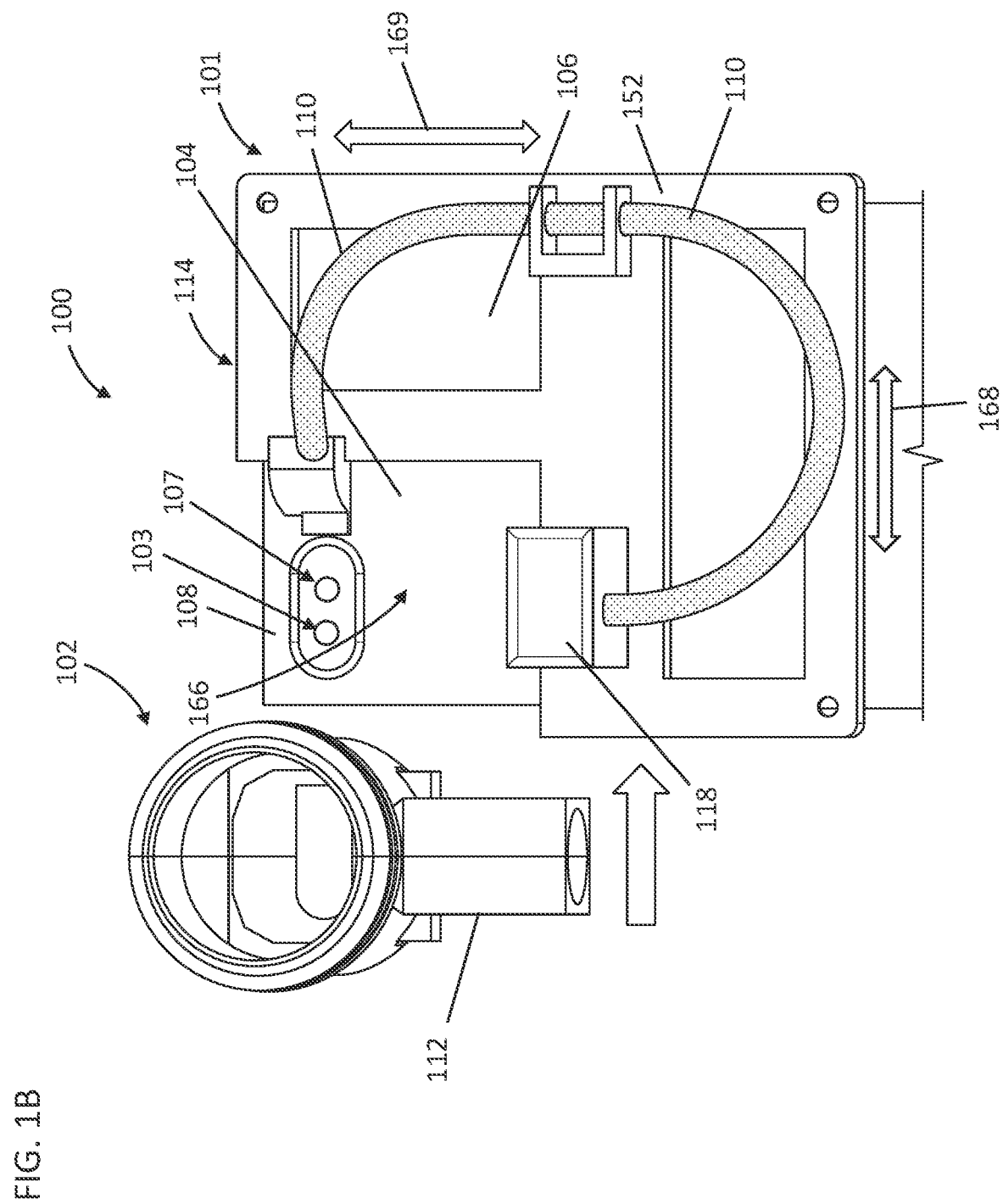
FIG. 1B is a front view of the system of FIG. 1A.

Disclosed herein are devices and methods for generating stereoscopic views of the fundus (or any anatomic structure) using a dual-camera portable computing device, where the camera lenses are coplanar and have different focal lengths. One variation of a system for generating stereoscopic views of the fundus of an eye may comprise a portable computing device having two cameras, and a detachable imaging system comprising an optical lens assembly and a portable computing device case configured to couple to the portable computing device such that the optical lens assembly is disposed over the two cameras. The portable computing device may be a dual-camera portable computing device (e.g., a smartphone having two cameras adjacent to each other), where the locations, orientations, lenses of the cameras are fixed. In one variation, the portable computing device may comprise a first camera having a first lens with a first focal length and a second camera having a second lens with a second focal length that may be greater than or equal to the first focal length. For example, the first lens may be a wide-angle lens while the second lens may be a telephoto lens. The relative locations of the first and second cameras may be fixed such that the first and second lenses are coplanar and/or their central axes (i.e., an axis that is perpendicular to the plane of the lens that passes through the center of the lens) may be parallel to each other. The first and second cameras may be separated from each other by a space having a predetermined length, which may be less than about 30 mm, e.g., about 8 mm, about 10 mm, about 10.5 mm, about 12 mm, about 15 mm, etc. One variation of an optical lens assembly may comprise an objective lens and a relay lens. The relay lens may act to provide each of the portable computing device cameras a distinct vantage point of this same retinal image provided by the objective lens. The relay lens may be sized to span across both cameras of the portable computing device. For example, the relay lens may have a diameter that is greater than or equal to the sum of the diameter of the first camera lens, the diameter of the second camera lens, and the separation distance between the first and second cameras. Because the two portable computing device cameras are located at a fixed distance apart from each other, they may acquire two sets of images from two distinct vantage points. Without wishing to be bound by theory, multiple vantage points of a fundus may be provided by a relay lens (or any spherical lens) because a relay lens may have a nearly infinite number of prisms, increasing in diopters as the distance from the center of the lens increases. A single relay lens having a diameter that is sufficiently large (e.g., greater than the combined diameters of the two lenses and the separation distance between them) may provide two distinct vantage points of the same image to each of the two cameras. When the images from the two cameras are combined, (e.g., viewed with the appropriate glasses), a 3-D image or view may be generated. An optical lens assembly comprising an objective lens and a single relay lens as described herein may allow images of an object (e.g., a patient's eye) to be acquired from multiple vantage points using a pair of coplanar cameras that are in relatively close proximity to the object.

In one variation, the optical lens assembly of the detachable imaging system may comprise an objective lens with an objective lens focal length and a relay lens with a relay lens focal length. The objective lens and the relay lens may be aligned such that their focal points are co-localized at a location or point between them, for example, at a location between the focal points of the first and second cameras. The relay lens may be sized to span across both cameras of the portable computing device. For example, the relay lens may have a diameter that is greater than or equal to the sum of the diameters of the two camera lenses of the portable computing device and the separation distance between the first and second cameras. In some variations, the relay lens focal length may be less than or equal to the difference between the second focal length and the objective lens focal length, and greater than the first focal length. The images captured by the first and second cameras through the optical lens assembly may be used to generate a stereoscopic view. In some variations, the objective lens may be detachably coupled to the optical lens assembly such that objective lenses with different optical properties (e.g., filters, focal lengths, etc.) may be used to image different aspects of the eye and/or different anatomic structure.

The detachable imaging systems described herein may, when disposed over two cameras of a portable computing device, provide image views to the cameras that may be combined to generate a stereoscopic or 3-D view of the back of the eye (e.g., fundus, retina). The detachable imaging system may also facilitate stereoscopic or 3-D viewing of smaller anatomic structures, and may provide some magnification of the anatomical structure. Such stereoscopic views or images may provide enough information to direct, guide, and/or counsel patients in primary care offices, community clinics, and/or rural locations around the world to seek appropriate care. For example, the detachable imaging systems described herein may be used to obtain stereoscopic images of the optic nerve head. The images acquired by the cameras of the portable computing device may be displayed on the portable computing device, and/or may be transmitted to a remote controller and/or display for viewing and analysis. In some variations stereoscopic viewing of the images may comprise using traditional stereoscopic or prismatic glasses or a stereoscope.

Since portable computing devices are widespread and generally available, a detachable imaging system such as any of those described below may provide additional optical functions that facilitate the acquisition of eye images (including stereoscopic views of the eye), thereby helping to improve access to eye screening. In addition, images acquired using the device and methods described herein may be electronically transmitted to remote eye care specialists for analysis and/or diagnosis. That is, even if individuals do not have access to the expertise of a local eye care specialist, they are able to seek and obtain medical advice from a remote specialist, which may help expedite the commencement and progress of treatment.

The illumination light to the eye may be provided by an external light source (e.g., a light-emitting diode mounted on the detachable imaging system and directed through the optical lens assembly to the eye), and/or provided by the portable computing device (e.g., one or more flash light sources located adjacent to and/or between the two cameras).

While the examples described and depicted below use a smartphone for the acquisition and processing of fundus images, it should be understood that the devices and methods described herein may be adapted for use with any portable computing device comprising two cameras at fixed positions relative to each other (and an optional visible light source) to acquire images of any portion of the eye. For example, the devices and methods described herein may be used with any type of portable computing devices, including but not limited to, smartphones, personal digital assistants (PDAs), cell phones, tablet PCs, phablets (personal computing devices that are larger than a smartphone, but smaller than a tablet) and the like, and portable or wearable augmented reality devices that interface with an operator's environment through sensors and may use head-mounted displays for visualization, eye gaze tracking, and user input. Light and/or image data detected by the portable computing device camera image sensors may be displayed in a view finder and/or preview frame (e.g., viewing window) of a portable computing device camera application. When a particular image view and/or light data and/or image data is to be saved, the user may trigger the camera to acquire the image by, for example, pressing a button, key, and/or graphic on a touch-sensitive screen of the portable computing device. Alternatively or additionally, the camera may be triggered to acquire an image by pressing a button or key located on an external housing of the portable computing device. In some variations, image acquisition may be triggered by an auto-capture algorithm, which may be stored in a memory of the portable computing device and executed by a controller of the portable computing device. One variation of an auto-capture mode may comprise detecting a pre-defined event or pre-defined pattern of events, and triggering the camera to acquire one or more images when the pre-defined event or pattern of events is detected. For example, in auto-capture mode, the camera may be triggered to acquire an image when it detects that the images in the preview frame is in focus, and/or when features of interest (e.g., optic nerve, fundus, etc.) are within the field-of-view of the camera(s). Additionally or alternatively, the cameras of the portable computing device variations may capture moving images or video.

Figure 2:
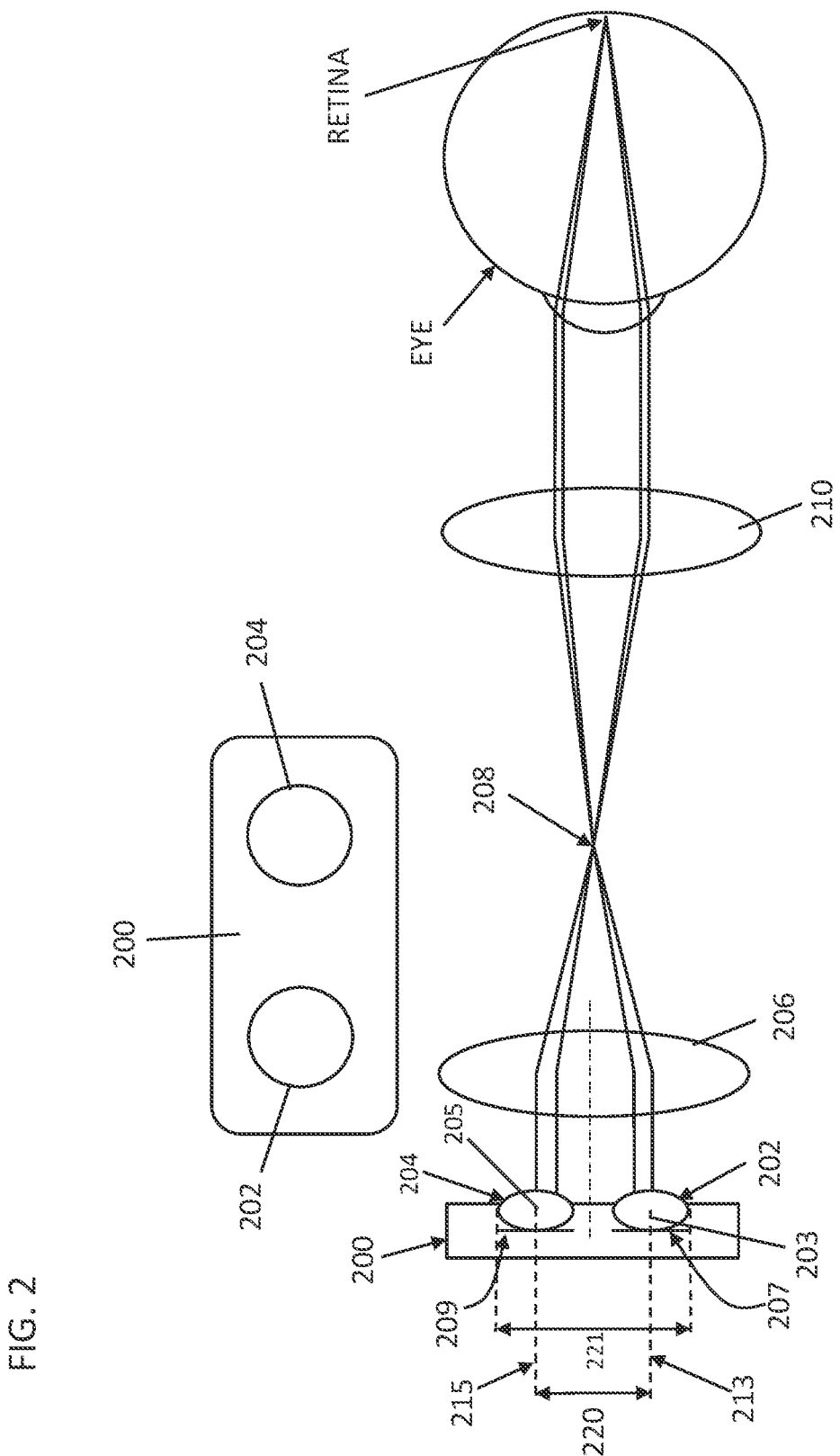
FIG. 2 is a schematic representation of an optical path for one variation of a system for acquiring images for generating stereoscopic views of the eye.

FIG. 2 is a schematic depiction of the optical paths and components of one variation of a detachable imaging system for generating stereoscopic views. The basic concept of stereoscopic imaging is that a single object is viewed or imaged by two cameras (simultaneously and/or sequentially) such that the object is viewed from two distinct vantage points. This "triangulation" (i.e., the triangle formed by a length between the two cameras and a length between the object and each of the two cameras individually) creates a triangle that may be used by the human brain to determine depth or distance. Depth may be determined by an algorithm or computer based system by overlaying the two images such that the degree of "blur" or offset of the same object in the two images may be indicative of the distance that object is from the cameras.

Typically, in order to create a triangle, the cameras are angled towards the object and at an angle relative to each other, and positioned such that they form an angle between them. That is, the central axes of the cameras (e.g., sensors or lenses) are usually at an angle to each other, and are not parallel to each other. Angling or tilting of the central axes of the cameras may allow two images of the optic nerve from two distinct triangulated points of roughly 10 degrees to be taken (e.g., simultaneously with two cameras or sequentially with one camera). This may produce two images of the same object from two vantage points and these images may be placed side by side on a display or viewing device for stereoscopic viewing of the optic nerve (e.g., using a pair of prism glasses).

In contrast, a coplanar pair of cameras (202, 204) on a portable computing device or smartphone (200) where their central axes (213, 215) are approximately parallel are not typically suitable for viewing micro environments that are in close proximity, e.g., fundus of an eye. This arrangement is often used for extracting 3-dimensional or depth information from macro environments, e.g., people and objects that are far away. However, the detachable imaging systems described herein may adjust the viewing optics of a portable computing device dual cameras such that relatively microscopic environments that are in close proximity to the cameras, and/or objects outside the focal range of the commercially available portable computing device cameras, may be viewed stereoscopically. A relay lens (206) and an objective lens (210) may facilitate triangulation and may optionally magnify a microscopic environment, which may place the image of the microscopic environment at a focal point (208) suitable for imaging by the portable computing device cameras. The relay lens may be sized to span across both cameras of the portable computing device. For example, the relay lens may have a diameter that is greater than or equal to the sum of the diameter of the first camera lens, the diameter of the second camera lens, and the separation distance between the first and second cameras. Accentuating the triangulation effect for stereoscopic viewing of close-proximity objects may be accomplished by a single relay lens that is disposed over both portable computing device cameras utilizing Prentice's Rule. Prentice's Rule describes that increasing the distance between the optical centers of each of the lenses (203, 205) may increase the prismatic effect (i.e., simulating or approximating the effect of one or more prisms disposed over the lenses). This prismatic effect may heighten or accentuate the triangulated imaging of the optic nerve using a coplanar or parallel set of two cameras such that each of the cameras acquire images of the optic nerve from two vantage points. The detachable imaging systems described herein may be used to image any anatomic structure, and in some variations, may also magnify the view, which may help facilitate the extraction of depth information.

The focal length of the relay lens may be selected based on one or more of the focal lengths of the first and second portable computing device cameras (202, 204), and/or the focal length of the objective lens (210), and/or the separation distance between the first and second portable computing device cameras, as will be explained further below.

Devices

FIGS. 1A and 1B depict one variation of a detachable imaging system for generating stereoscopic views of an eye (e.g., fundus). The detachable imaging system (100) may comprise a portable computing device case, an optical lens assembly (102) attached to portable computing device case, and a light emitter optically connected to the optical lens assembly. The light emitter may be mounted on the portable computing device case. The optical lens assembly (102) may be detachable from the computing device case. In some variations, the light emitter may comprise a light guide (110) optically connected to the optical lens assembly (102) (when it is attached to the case) and also optically connected to a light source on the portable computing device (e.g., a flash light source) to channel that light to the optical lens assembly. The light guide may be, for example, one or more fiber optic cables.

Figure 1C:
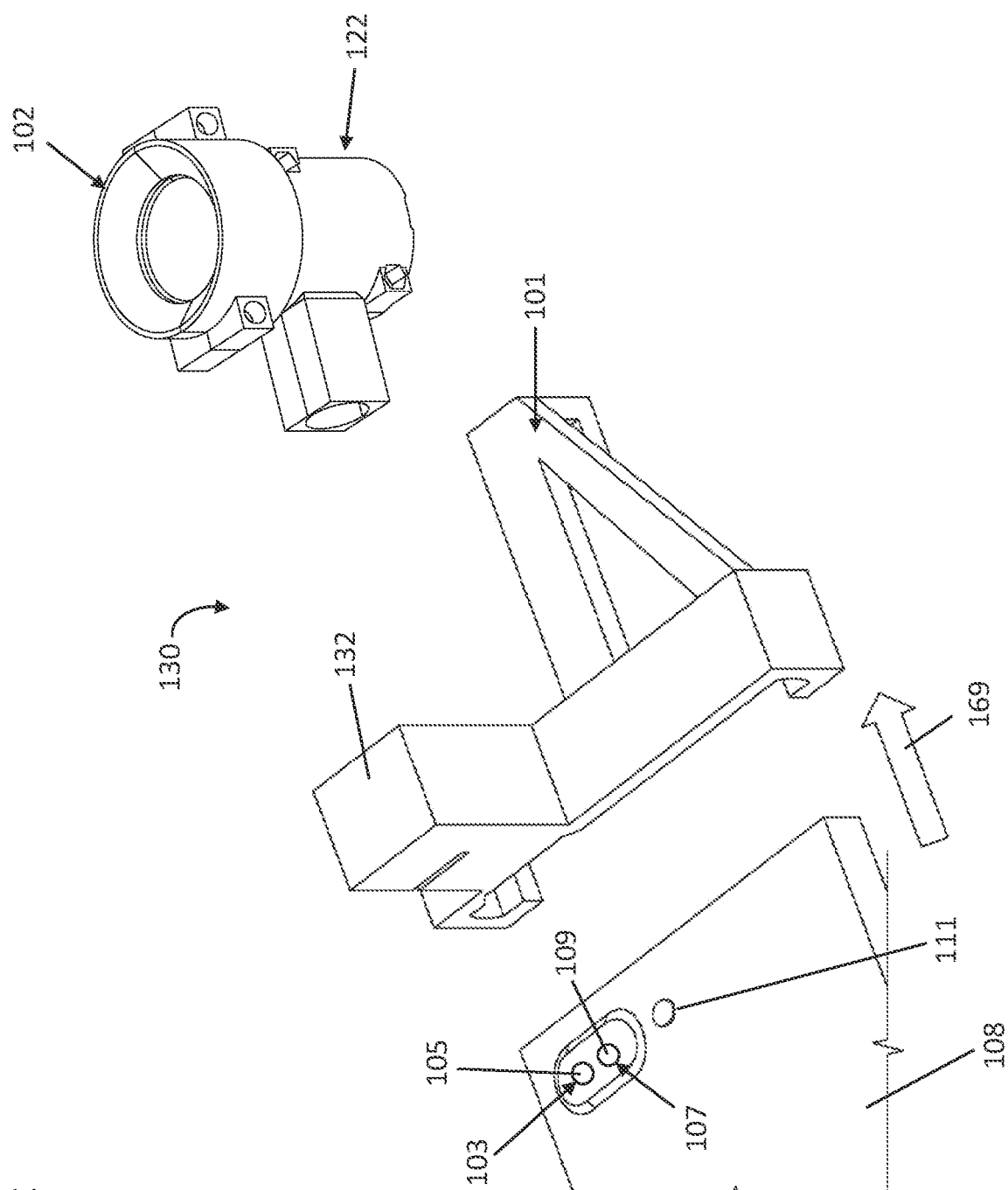
FIG. 1C is a perspective view of one variation of a system for acquiring images for generating stereoscopic views of the eye.
Figure 1D:
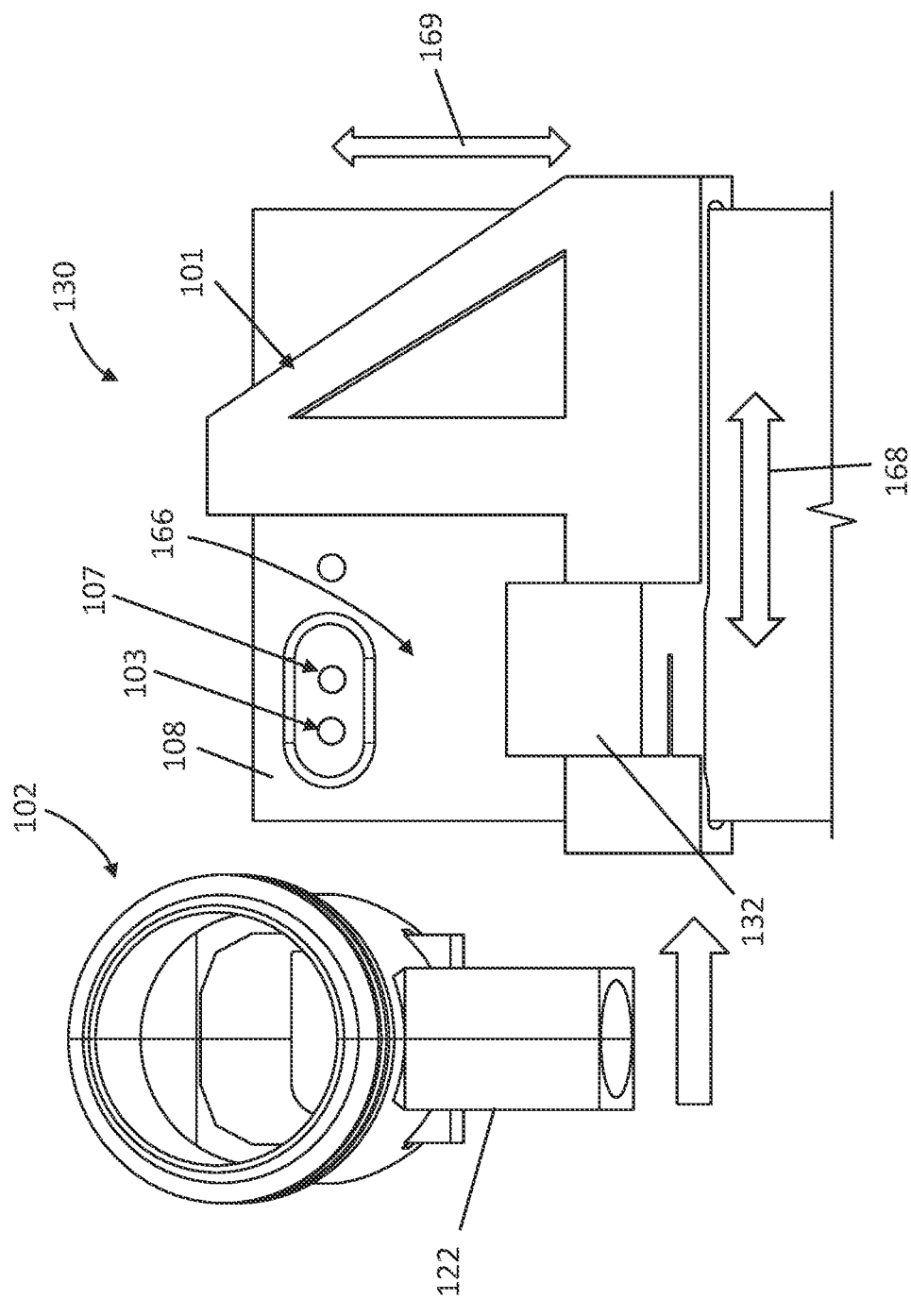
FIG. 1D is a front view of the system of FIG. 1B.

Alternatively or additionally, such as in the variation of a detachable imaging system (130) depicted in FIGS. 1C and 1D, the light emitter may comprise a light source such as one or more light-emitting diodes located within a housing (132) on the portable computing device case (101). The light source may comprise a red and/or near-infrared (NIR) light source (e.g., from about 580 nm to about 1200 nm, about 530 nm to about 650 nm, about 680 nm to about 750 nm), and/or may comprise a UV light source (e.g., having wavelengths from about 100 nm to about 400 nm), and/or may comprise a blue light source (e.g., having wavelengths from about 450 nm to about 500 nm), and/or a green light source (e.g., having wavelengths from about 500 nm to about 570 nm), etc. The housing (132) may also be an optical lens assembly mount to which the optical lens assembly (102) may be attached, and the light source may be located in a position to channel illumination light to the optical lens assembly.

Figure 7A:
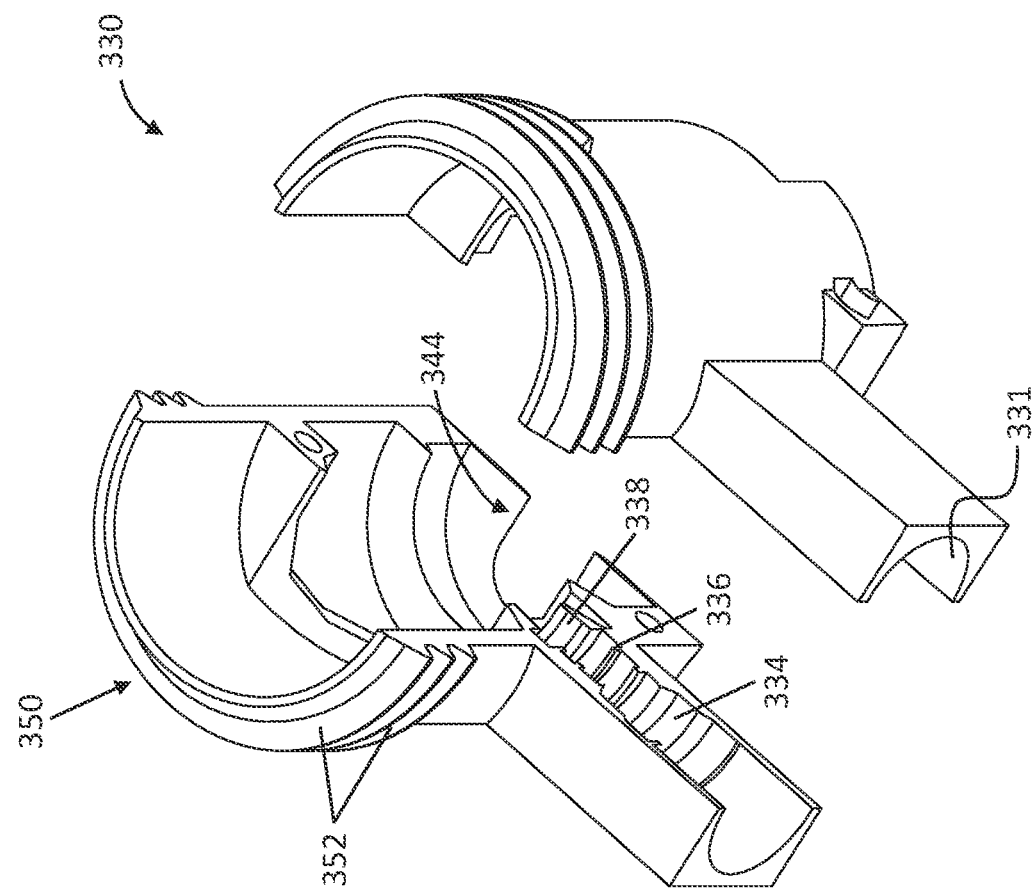
FIG. 7A is a perspective cutaway view of one variation of an optical lens assembly housing.
Figure 7C:
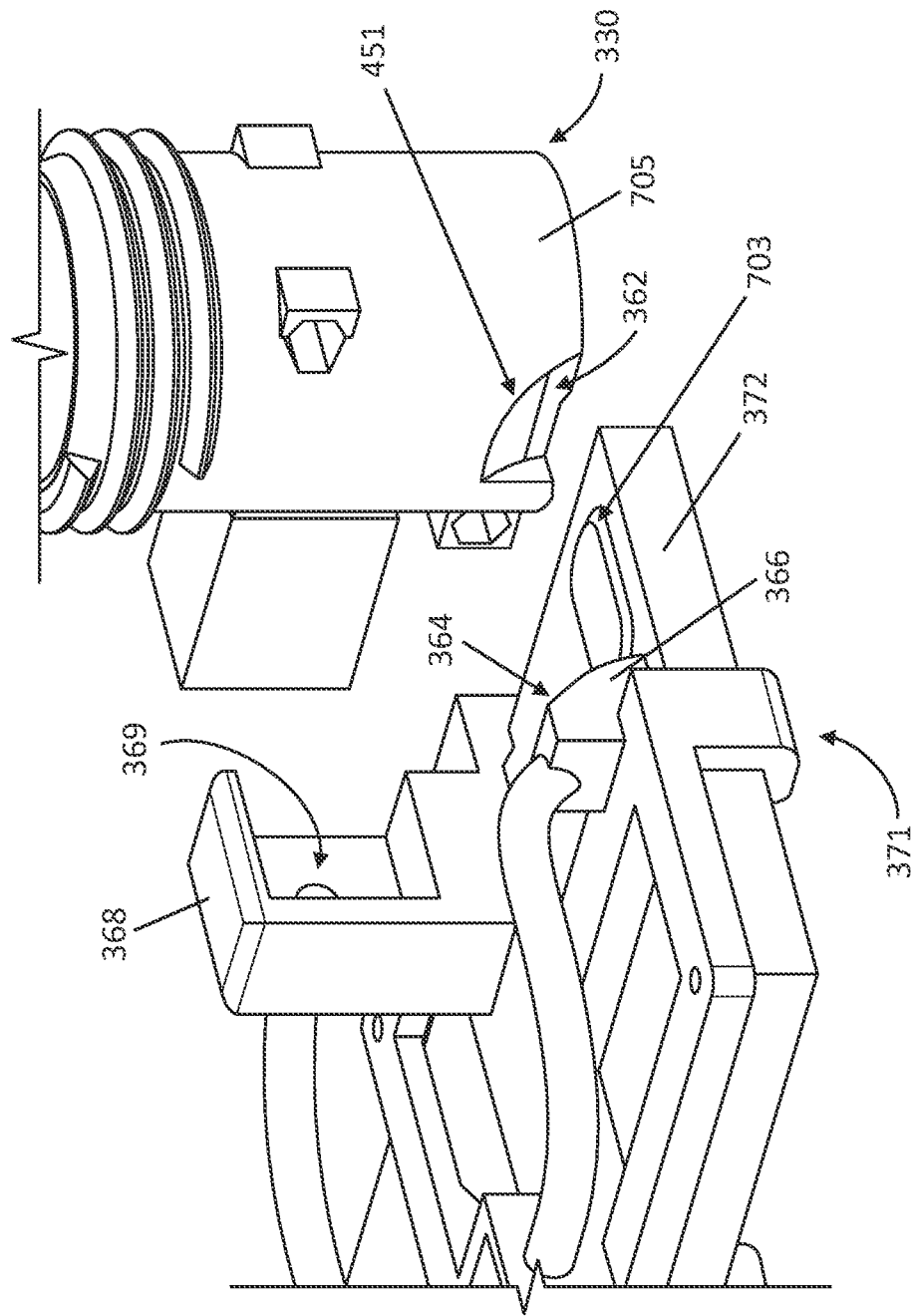
FIG. 7C is a perspective left-side view of an optical lens assembly and a portion of a portable computing device case.

The optical lens assembly (102) may be enclosed in an optical lens assembly housing, such as the housing (112) for the variation depicted in FIGS. 1A and 1B, or the housing (122) for the variation depicted in FIGS. 1C and 1D. The light emitter may be mounted on and/or enclosed in a portable computing device housing or case, such as the case (114) for FIGS. 1A and 1B or the case (101) for FIGS. 1C and 1D. The optical lens assembly housing may be detachably coupled to the portable device case. For example, the portable computing device case may comprise an optical lens assembly mount (118, 132) having a recess that is configured to receive a portion of the optical lens assembly housing such that light from the light emitter (e.g., light source and/or light guide) may be directed through the optical lens assembly (102) toward a patient's eye. FIG. 7C depicts one example of an optical lens assembly mount (368) having a recess (369) to receive optical lens assembly housing (330). Optionally, in some variations, an optical lens assembly may comprise a light source splitter located in a portion of the optical lens assembly housing that is, when coupled to the portable computing device case, in optical connection with the light source and/or the light guide. The optical lens assembly may comprise one or more optical components, such as various polarity filters (e.g., S-phase and P-phase filters), beam splitter(s), and/or relay lenses, and/or objective lenses that may help to alleviate unwanted glare.

In some variations, all of the components of the detachable imaging system may be enclosed in a single housing and/or integrated on a single mounting substrate, in other variations, the different components may be grouped and enclosed in separate housing modules, which may be assembled at the time of use by the clinician or technician. For example, components that may be relatively less expensive to manufacture and/or may change as portable computing devices are updated may be included in a housing separate from components that remain largely the same (or unchanged) across portable computing device updates and/or may be relatively more expensive to manufacture. For example, the optical lens assembly may remain the same across multiple portable computing devices while the case (e.g., attachment feature) may change across different portable computing device types and updates. In one variation, a detachable imaging system may comprise an optical lens assembly and a portable computing device case, where the optical lens assembly is detachable from the portable computing device case. The optical lens assembly itself may also comprise detachable optical modules, which may facilitate optical adjustments and customizations, as may be desired.

Figure 1E:
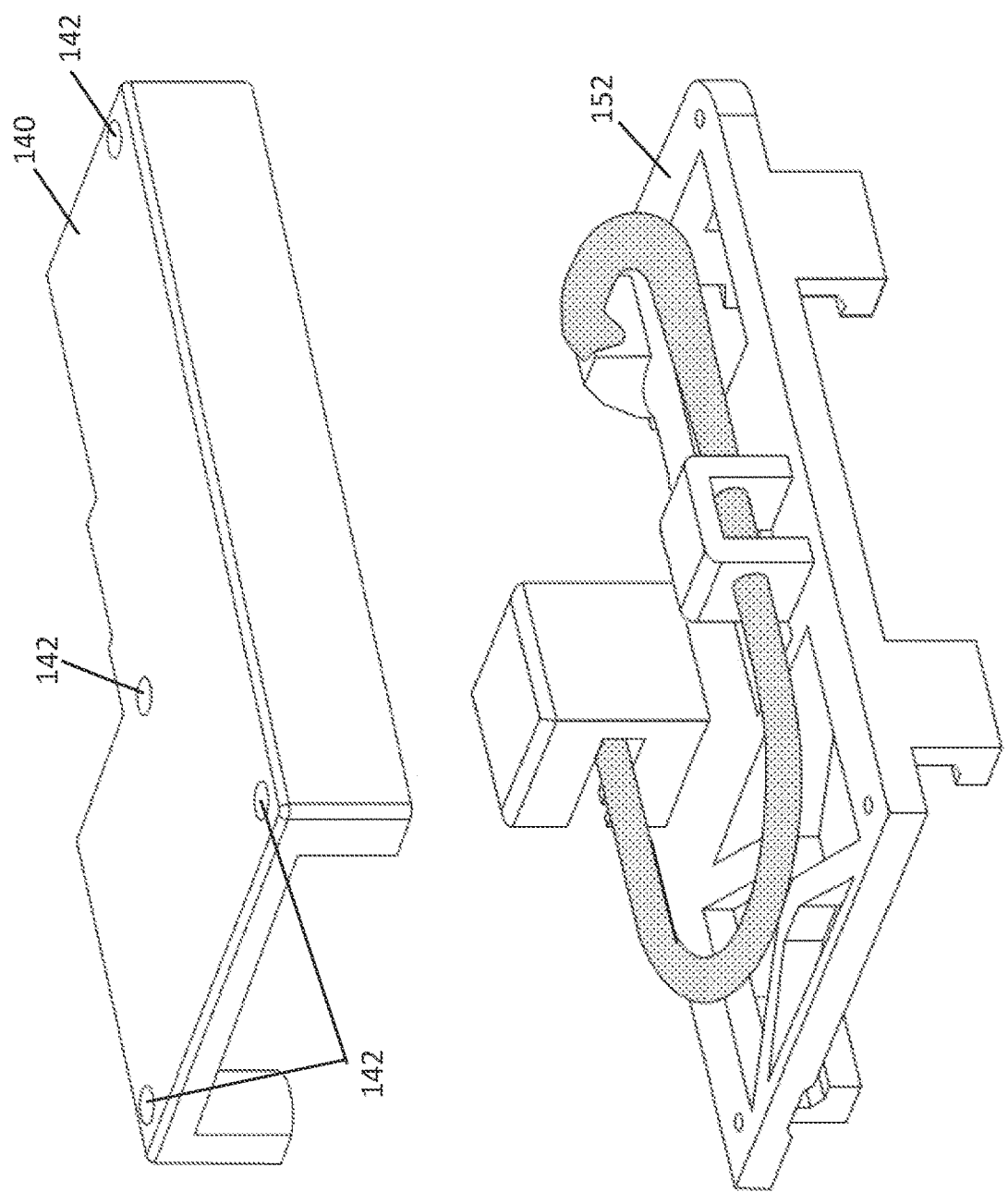
FIG. 1E is a side perspective view of one variation of portable computing device case with a shell or housing for enclosing components of the portable computing device case.

The detachable imaging system may comprise a shell that encloses the light emitter and various mount structures of the portable computing device case. FIG. 1E depicts one variation of a shell (140) that may be configured to fit over the frame and to enclose the components of the portable computing device cases depicted in FIGS. 1A-1D. Shell (140) may fit over the frame (152) and may be attached to the frame (152) via one or more screws (not shown) and threaded bores (142). A shorter variation of the shell (140) may be used for enclosing the components of the portable computing case (101) depicted in FIGS. 1C and 1D. In some variations, the shell may be large enough to enclose the portable computing device (e.g., smartphone). Alternatively or additionally, some variations may comprise a second shell that encloses a smartphone and retains it within the device case such that the smartphone is enclosed with only the screen viewable and accessible from outside the second shell. While the variations described herein comprise a portable computing device case that allows for slidable attachment and removal of a computing device (e.g., without additional or specialized tools or adhesives, without excessive force, etc.), it should be understood that in other variations, the portable computing device may be fixedly coupled to the case. In such variations, the portable computing device may be secured to the case using one or more adhesives, screws and threaded bores, and/or may be secured to the case by welding, soldering, and the like.

Portable Computing Device Cameras

The detachable imaging systems (100, 130) of FIGS. 1A-1D may be configured to be coupled to a portable computing device (108) comprising a first camera (103) having a first image sensor and a first camera lens (105) disposed over the first image sensor, and a second camera (107) having a second image sensor and a second camera lens (109) disposed over the second image sensor. Optionally, the portable computing device may have and one or more light sources (111) (e.g., a flash light source). Each of the first and second cameras may comprise an image sensor and a lens disposed over the image sensor. The focal length of the first lens of the first camera may be different from the focal length of the second lens of the second camera. For example, one camera lens may be a telephoto lens while the other camera lens may be a wide angle lens. In some variations, the focal length of the first lens of the first camera and the focal length of the second lens of the second camera may be the same. The first and second cameras may also be optically coplanar; that is, their lenses may be positioned such that their central axes are parallel, and/or the lens faces are coplanar, and/or the central planes of the lenses are coplanar. The first and second lenses may be substantially parallel to the planes of the image sensors, and are not tilted with respect to the planes of the image sensors. The diameters of the first and second camera lenses may be the same (e.g., as depicted throughout this document) or may be different (e.g., where one lens has a larger diameter than the other). The portable computing device may also optionally comprise a light source (e.g., a flash light source). The portable computing device may be a smartphone, personal digital assistant (PDA), cell phone, tablet PC, phablet (personal computing devices that are larger than a smartphone, but smaller than a tablet) and the like, and portable or wearable augmented reality devices that interface with an operator's environment through sensors and may use head-mounted displays for visualization, eye gaze tracking, and user input.

Optical Lens Assembly

One variation of a detachable imaging system for stereoscopic views of an eye may comprise an optical lens assembly that is configured to direct illumination light to the eye and to capture and/or optically modify light returning from the eye for acquisition by first and second cameras of a portable computing device, such as any of the portable computing devices described above. One variation of an optical assembly may comprise an objective lens, one or more optical components for providing illumination to the eye (i.e., illumination optical components) through the objective lens, one or more optical components that collect light through the objective lens for imaging (i.e., imaging optical components), and a beam splitter that separates illumination light to the eye and imaging light returning to from the eye. In one variation, the optical lens assembly may comprise a relay lens that is configured to be disposed over the first and second cameras of the portable computing device. The relay lens may be sized to span across both cameras of the portable computing device. For example, the relay lens may have a diameter that is greater than or equal to the sum of the diameter of the first camera lens, the diameter of the second camera lens, and the separation distance between the first and second cameras. The focal length of the relay lens may be adjusted so that images acquired by each of the first and second cameras may be used to generate a stereoscopic (e.g., a 3-D) view or image. The focal length of the relay lens may depend on the focal length of at least one of the first and second camera lenses in combination with the focal length of the objective lens. For example, the sum of the focal lengths of the relay lens and the objective lens may be between the focal lengths of the first and second lenses of the portable computing device cameras. In some variations, the sum of the focal lengths of the relay lens and the objective lens may approximate the larger focal length of the two camera lenses. In still other variations, where the first camera has a first lens with a first focal length and the second camera has a second lens with a second focal length that is longer than the first focal length, the relay lens focal length may be less than or equal to the difference between the second focal length and the objective lens focal length, and greater than the first focal length. The optical lens assembly may also comprise one or more optical components and arrangements to help reduce glare from the eye. The optical lens assembly may also comprise one or more optical components (e.g., beam splitters) that may direct illumination light with different wavelengths to the eye.

Figure 3A:
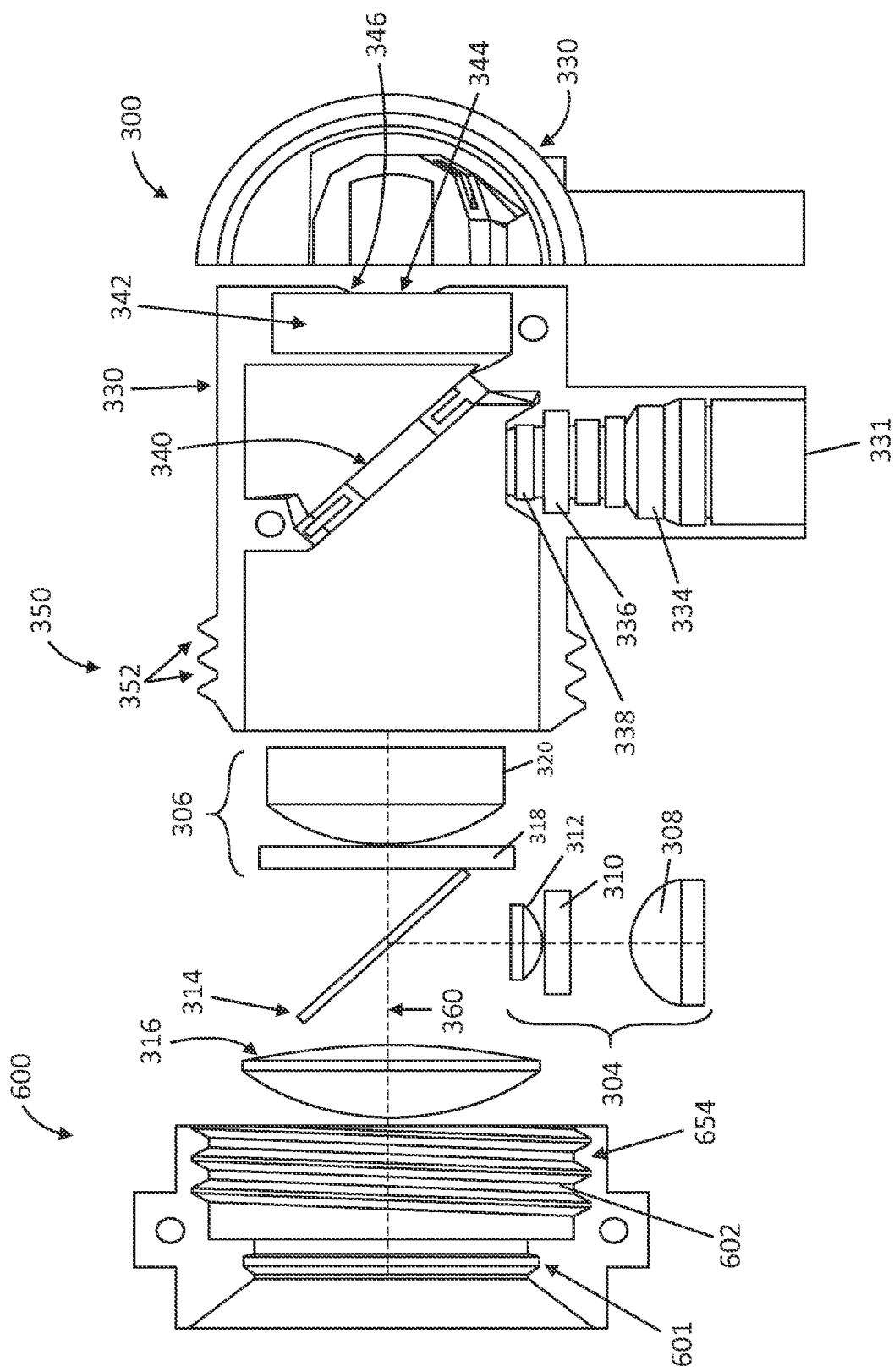
FIG. 3A is a partial cutaway side view and a front view of one variation of an optical lens assembly.
Figure 3B:
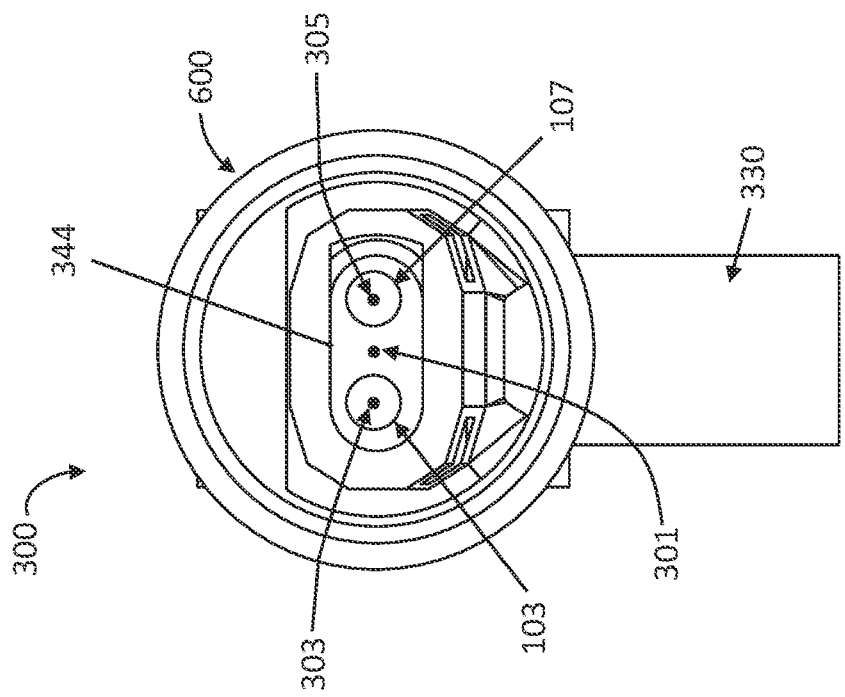
FIG. 3B is a front view of one variation of an optical lens assembly.
Figure 4A:
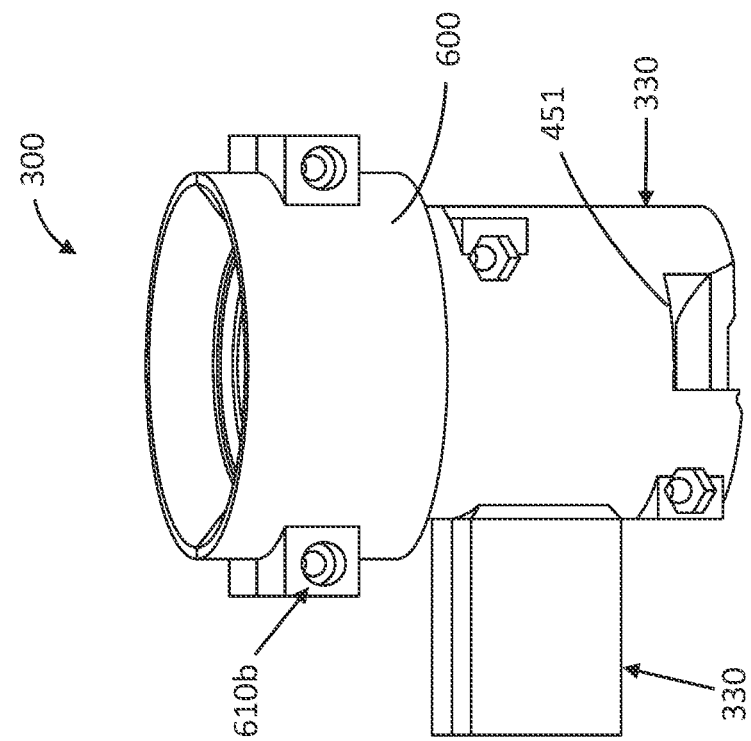
FIGS. 4A-4D depict perspective, side, partially-exploded, and close-up views of one variation of an optical lens assembly housing (e.g., which may be used with the system depicted in FIGS. 1A-1B).
Figure 4B:
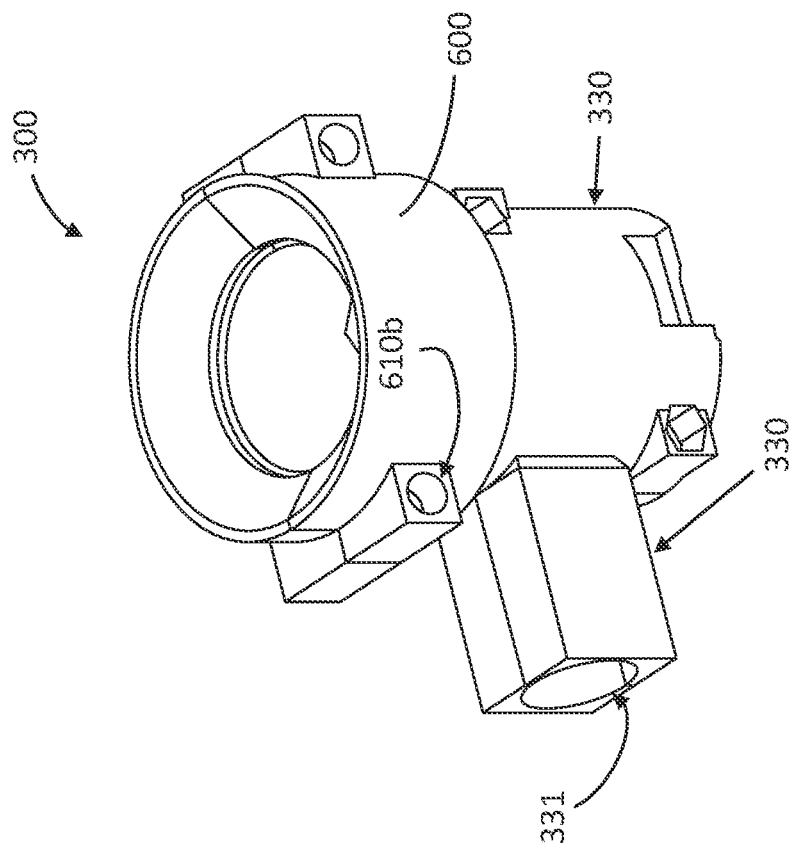
Figure 4D:
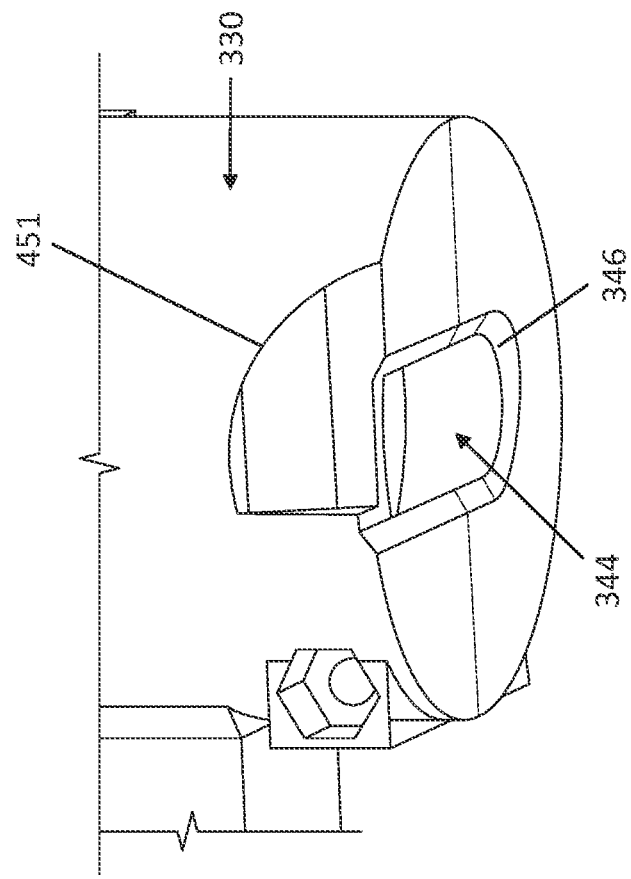
Figure 4C:
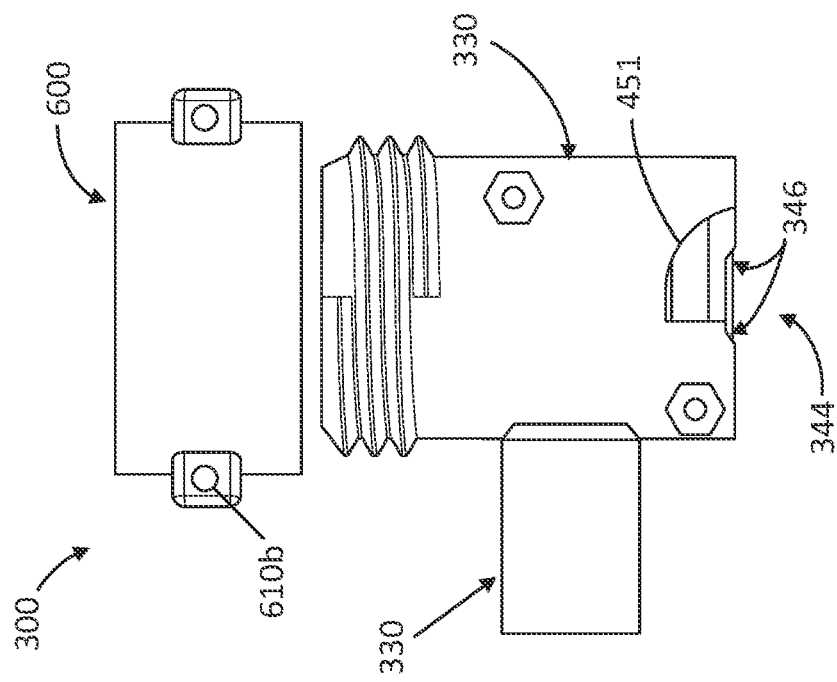
Figure 5B:
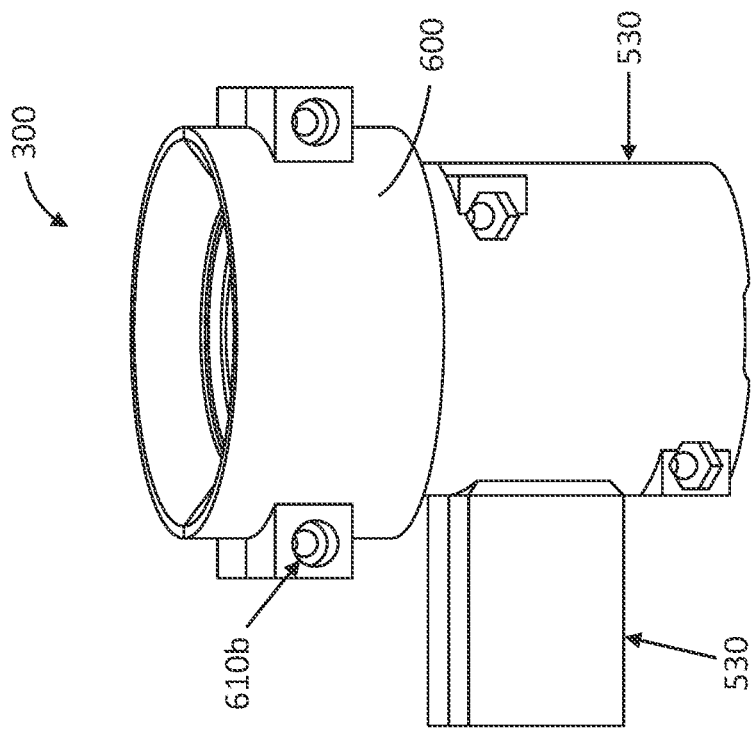
FIGS. 5A-5D depict perspective, side, partially-exploded, and close-up views of one variation of an optical lens assembly housing (e.g., which may be used with the system depicted in FIGS. 1C-1D).
Figure 5A:
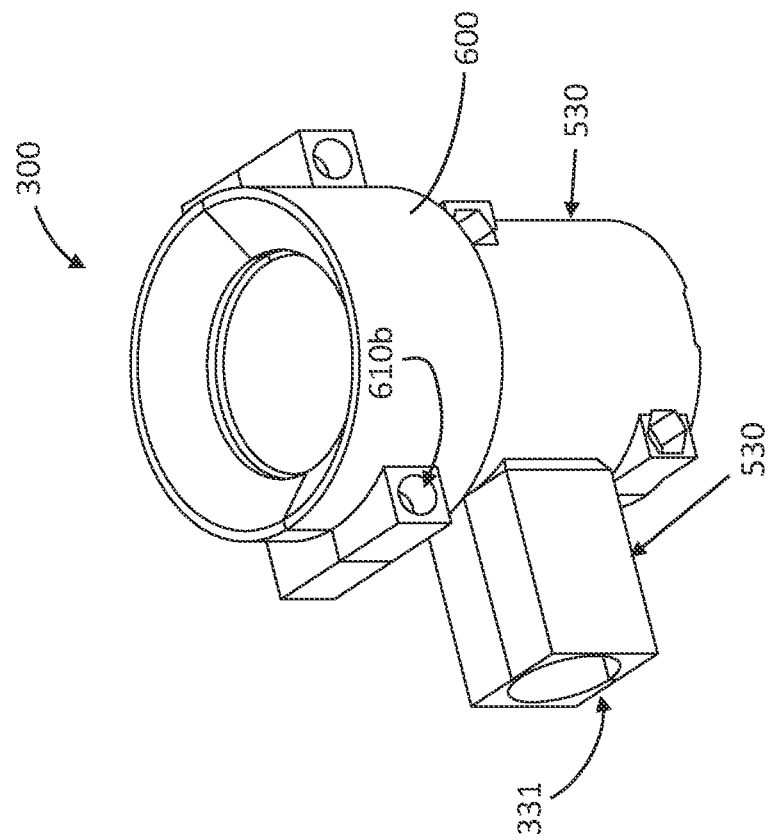
Figure 5D:
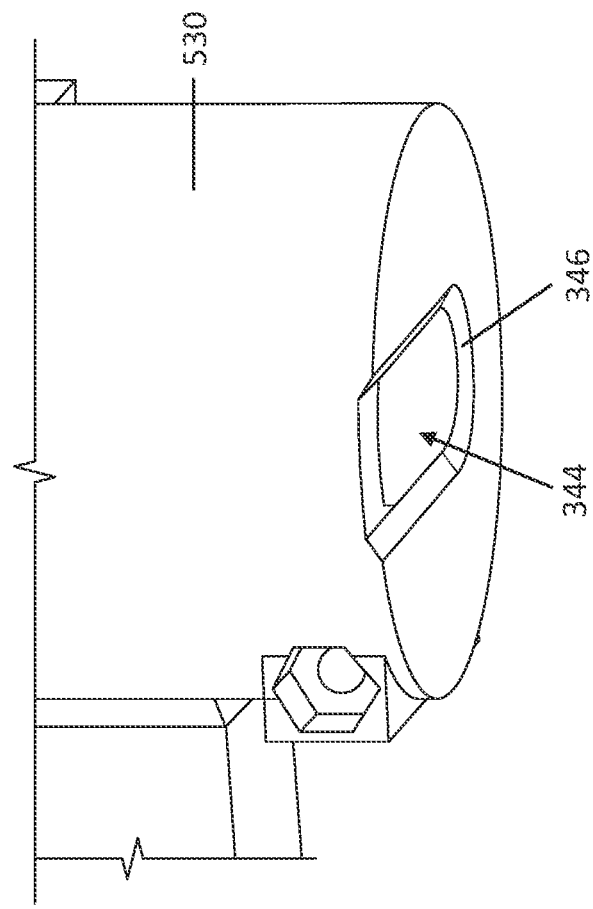
Figure 5C:
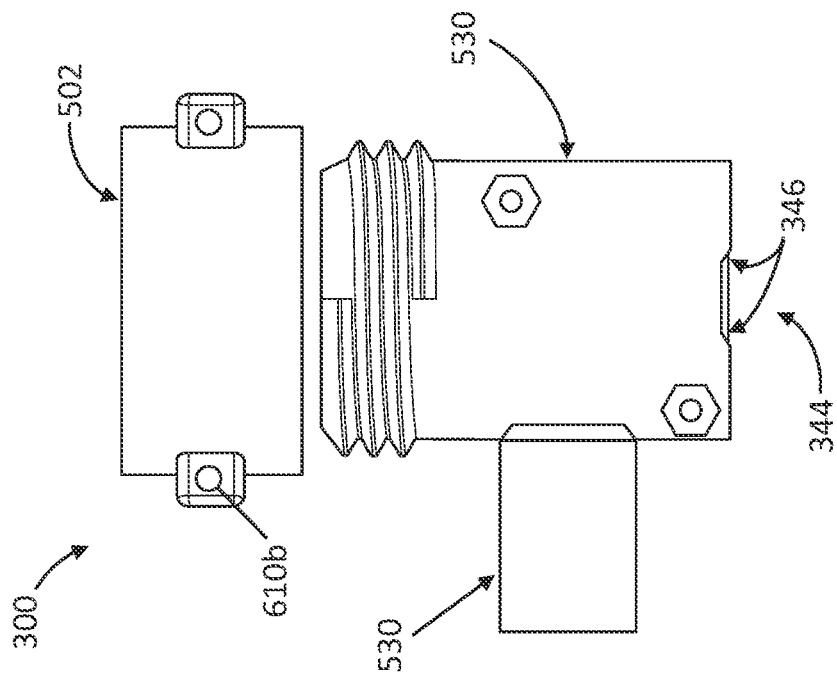

FIG. 3A is an exploded side and front view of one variation of an optical lens assembly. FIG. 3B is a front view of the optical lens assembly, from the perspective of the object (e.g., eye) that is being imaged. An optical lens assembly may comprise illumination optical components (304) and imaging optical components (306) of an optical lens assembly (300). Illumination optical components (304) may comprise a collector lens (308) and a polarizing filter (310). Optionally, illumination optical components (304) may comprise an optional condenser (312) and a light guide/emitter and/or light source (not shown). The collector lens (308) may collimate light from a light emitter, such as light guide and/or light source (e.g., from a NIR and/or a visible light or white light LED, and/or from a light guide such as a fiber optic cable carrying light from the light source/flash of a smartphone), and may, for example, comprise a lens having a diameter of about 15-30 mm and a focal length of about 12-20 mm. The polarizing filter (310) may transmit light having a particular phase while blocking light with a different (e.g., orthogonal or perpendicular or opposite phase), where the phase of light that is transmitted is aligned with (e.g., matches) the phase of light that is reflected by the beam splitter. For example, the polarizing filter (310) may transmit S-phase light (i.e., block P-phase light) to the polarizing beam splitter (314), which may reflect S-phase light. In some variations, the polarizing filter (310) may comprise a glass linear polarizer having a diameter of about 12-30 mm. The optional condenser (312) may be configured to focus the S-phase light from the polarizing filter (310) onto the polarizing beam splitter (314), and may comprise a lens having a diameter of about 9-20 mm and a focal length of about 20-50 mm. S-phase illumination light from the condenser (312) may be reflected by the polarizing beam splitter (314) and directed to an objective lens (316) toward a patient's eye. The polarizing beam splitter (314) may have any size, and may be configured to reflect light of one phase and transmit light of another phase (e.g., orthogonal or perpendicular or opposite phase). In this variation, the polarizing beam splitter (314) reflects S-phase light and transmits P-phase light, which turns the illumination light from the condenser by about 90° to direct it to the objective lens (316), and may comprise a square glass substrate polarizer having a length/width from about 12.5 mm to about 25 mm. The proportion of light that is reflected and the proportion of the light that is transmitted by the polarizing beam splitter (314) may also vary and may, for example, be about 90% reflected and about 10% transmitted, or may be about 50% reflected and about 50% transmitted, or may vary up to about 99% reflected to about 1% transmitted. Light from the eye returning through the objective lens (316) may pass through the polarizing beam splitter (314) and the imaging optical components (306) before the light is acquired by the camera image sensor(s) of the portable computing device (e.g., smartphone). One variation of imaging optical components (306) may comprise a second polarizing filter (318) and a relay lens (320). As indicated above, the polarizing beam splitter (314) transmits P-phase light (and reflects or blocks S-phase light), so the light that passes through the relay lens (320) is P-phase light. In other variations, the polarity of the filters and polarizing beam splitter may be reversed. Such a "cross-polarization" arrangement of optical components between the illumination light and imaging light may help to reduce glare and/or light scatter or noise that may arise from the illumination light. The second polarizing filter (318) may provide additional filtering to further reduce glare. For example, the second polarizing filter (318) may be transmit P-phase light and may comprise a glass linear polarizer having a diameter from about 12 mm to about 40 mm. It should be understood that in other variations, the polarities of the filters and beam splitters described above may be reversed.

In some variations, illumination to the patient's eye may be provided by the illumination optical components (304) along an illumination axis. The light returning from the eye may propagate along an imaging axis (360) that may be co-linear with the illumination axis, as depicted in FIG. 3A. The centers of the objective lens (316), the relay lens (320) and optionally the polarizing filter 318 may be aligned along the imaging axis. While the imaging axis (360) may be generally parallel to the central axes of each of the two portable computing device cameras, the imaging axis may not be co-linear with either of the camera central axes. This may help to reduce the effect of glare on each of the cameras, which may be exacerbated if the illumination axis, imaging axis, and camera central axes were co-linear. Referring to FIG. 3B, the illumination axis and the imaging axis (360), which may be perpendicular to the plane defined by the two portable computing device cameras (103, 107), may intersect with the portable computing device at a point (301). The central axis of the first camera (103) may be represented by point (303) and the central axis of the second camera (107) may be represented by point (305), where the central axes are perpendicular to the plane of the cameras. Residual or scattered light from the illumination light path may generally aggregate around point (301), which may help reduce any glare that may affect the images acquired by the first and second cameras.

Optical Parameters of the Relay Lens

The relay lens (320) may have a focal length such that images from different vantage points may be acquired by the first and second portable computing device (e.g., smartphone) imaging sensors to generate a stereoscopic or 3-D view. The relay lens may be sized to span across both cameras of the portable computing device. For example, the relay lens (320) may have a diameter that is greater than or equal to the sum of the diameters of the first and second camera lenses and the separation distance between the first and second cameras (i.e., distance between the inner edges of the lenses). In some variations, the relay lens diameter may be greater than or equal to the distance between the outer edges of the first and second camera lenses. For example, the relay lens (320) may have diameter from about 15 mm to about 50 mm (e.g., from about 25 mm to about 35 mm, about 30 mm), where the diameters of each of the camera lenses may be from about 2 mm to about 15 mm, e.g., about 2 mm to about 3 mm, with a separation distance from about 3 mm to about 20 mm, e.g., about 5 mm, about 10 mm, etc. The relay lens may have a focal length such that an image resolution reduction for one camera is balanced against a field-of-view reduction for the other camera, for example. The relay lens focal length may be between the focal lengths of the first and second smartphone camera lenses. For example, the relay lens focal length may be less than or equal to the focal length of the second smartphone camera lens (i.e., for smartphone cameras having a first camera with a first focal length and a second camera with a second focal length that is longer than the first focal length). The relay lens focal length may also be selected so that a variety of objective lenses with different diopter values may be used without substantially disrupting the overall field-of-view. For example, a relay lens with a focal length of about 30 mm disposed over the cameras of a smartphone (e.g., one camera with a focal length of about 28 mm and the other camera with a focal length of about 56 mm) may be used in conjunction with a 70 diopter objective lens and/or with a 40 diopter objective lenses. In some variations, the focal length of the relay lens may be greater than or equal to the difference in the focal length of the objective lens and the greater of the two focal lengths of the smartphone camera lenses. In some variations, the focal length of the relay lens may be greater than or equal to the lesser of the two focal lengths of the smartphone camera lenses and less than or equal to the greater of the two focal lengths of the smartphone camera lenses. For example, a smartphone may comprise a first camera having a first lens with a focal length of about 28 mm and a second camera having a second lens with a focal length of about 56 mm. The objective lens of an optical assembly may have a focal length of about 18.5 mm. The relay lens of such optical lens assembly may have a focal length of from about 30 mm to about 40 mm, e.g., about 30 mm, about 37.5 mm (i.e., the difference between the focal lengths of the second camera lens and the objective lens, that is, 56 mm-18.5 mm=37.5 mm). In other variations, the focal length of the relay lens may be from about 20 mm to about 50 mm, and may be adjusted to balance the desired field-of-view with the resolution of the images acquired by the first and second image sensors. The location of the relay lens (320) within the optical lens assembly housing may be selected such that the relay lens is disposed directly over, and in some variations, in contact with, the surfaces of first and second smartphone camera lenses. The relay lens (320) and the objective lens (316) may be positioned such that their central axes are aligned, and their common central axis is aligned with a midpoint between the two cameras of the smartphone.

FIG. 2 is a schematic depiction of the relative arrangement of the relay lens and objective lens of an optical lens assembly that may help facilitate the acquisition of images by the first and second cameras of a portable computing device (e.g., a smartphone (200)) for generating a stereoscopic view. The smartphone (or any portable computing device) may comprise a first camera (202) having a first lens (203) and a first image sensor (207) located behind the first lens (203) and a second camera (204) having a second lens (205) and a second image sensor (209) located behind the second lens (205)). The first camera (202) and the second camera (204) may be located adjacent to each other, separated by a distance of (220) (from the center of the first lens (203) and the center of the second lens (205)). The first and second cameras may also be optically coplanar; that is, the lenses may be positioned such that their central axes are parallel and their lens faces are coplanar, and/or the central planes of the lenses are coplanar. The first and second lenses may be substantially parallel to the planes of the image sensors, and are not tilted with respect to the planes of the image sensors. An optical lens assembly may comprise a relay lens (206) disposed in front of the first and second cameras, and an objective lens (210) disposed in front of the relay lens. The relay lens (206) may be located directly over, and in some variations, in contact with, the surfaces of first and second smartphone camera lenses. The relay lens (206) may be arranged such that it has the same focal point (208) as the objective lens (210). For example, to view a fundus region or retina in an eye, the objective lens (210) may be selected and/or adjusted such that focal point (208) is at a location that coincides with the focal point of the relay lens (206). The optical characteristics of the relay lens and/or the objective lens may be selected to augment a prismatic effect such that the views of the image at the focal point (208) acquired by each of the first and second cameras are sufficiently offset from each other to generate a stereoscopic or 3-D view. In one variation, the objective lens may be a 54 diopter objective lens and the relay lens may have 30 mm focal length, which together, may help to preserve image resolution while maintaining a desired field-of-view. There may be an inverse relationship between relay lens focal length and image resolution as captured by an image sensor. The relay lens may be a single lens with a diameter that is greater than or equal to the distance between the outer edges of the two camera lens (221), i.e., the sum of the diameters of the two camera lenses and the separation distance between their two inner edges. This may augment the prismatic effect of the relay lens as the distance (220) between the central axes (213, 215) of the cameras increases. Certain optical distortions may be mitigated by increasing the diameter of the relay lens such that radius of curvature of the relay lens is decreased for the same focal length, which may help to decrease aberrations and increase image quality.

Optical Lens Assembly Housing

The optical lens assembly may comprise a housing comprising a plurality of grooves, slots, recesses, protrusions, notches, and the like for retaining the optical components described above. FIG. 3A depicts an exploded side view of one variation of an optical lens assembly (300) comprising an optical lens assembly housing (330), illumination optical components (304) and imaging optical components (306). The illumination optical components (304) may comprise a collector lens (308), a polarizing filter (310), and a condenser (312). Optionally, some lens assemblies may comprise an illumination light beam splitter, which may direct light from different light sources or emitters to the light path of the illumination optical components. As depicted in FIGS. 3A and 7A, the housing (330) may comprise a first recess (334) sized and shaped to retain the collector lens (308), a second recess (or slot) (336) sized and shaped to retain the polarizing filter (310), and a third recess (338) sized and shaped to retain the condenser (312). The housing (330) may have a diagonal slot (340) located above the third recess (338), the diagonal slot (340) configured to retain a polarizing beam splitter (314) that directs the light from the illumination optical components (304) to the objective lens (316) (and onward to a patient's eye). The housing (330) may also comprise one or more grooves, slots, recesses, protrusions, notches, and the like for retaining the imaging optical components (306), such as the second polarizing filter (318) and the relay lens (320). The housing (330) may comprise a groove (342) that is sized and shaped to retain both the second polarizing filter (318) and the relay lens (320). The groove (342) may have an opening (344) where the imaging light passes through the relay lens (320) to the imaging sensor of the portable computing device (e.g., smartphone). The opening (344) may comprise a beveled edge (346) around the circumference of the opening (344) (FIG. 2D). Alternatively or additionally, the opening (344) may be located in a notch (345), where the notch comprises a beveled edge (346), as depicted in FIG. 7B. The beveled edge may have an angle and/or edge thickness that may be configured to engage smartphones that have a camera lens that protrudes from the smartphone housing. The beveled edge may also help provide additional shielding from light emanating from an adjacent smartphone flash light source and/or ambient light/glare entering around the smartphone camera lens, which may help improve image quality. In addition, as will be described in greater detail below, the beveled edge may also track and/or contour around a protruding lens of a smartphone camera to provide an anchor point for the optical lens assembly housing to lock over the smartphone housing (when used in conjunction with the portable computing device case of the imaging system).

The optical lens assembly housing (330) of FIGS. 4A-4D may comprise a groove (451) having a curved contour (e.g., concave), which may correspond with a curved contour (e.g., convex) of an optical cable mount of the portable computing device case, as will be described later on and depicted in FIG. 7C. The optical lens assembly housing (330) may be used with a detachable imaging system that has an optical fiber that directs light from the computing device light source into the optical lens assembly for illuminating the eye. FIGS. 5A-5D depict one variation of an optical lens assembly housing (530) that may be used with a detachable imaging system that has a light source (separate from any light source of the portable computing device), such as an LED, that supplies light into the optical lens assembly for illuminating the eye. In contrast with the optical lens assembly (330), the optical lens assembly housing (530) does not have a groove (451).

The objective lens (316) may comprise an ophthalmic examination lens between about 30 diopters and about 80 diopters, for example, a 54 diopter ophthalmic examination lens with a 18.5 mm focal length, and may be located about 38.5 mm away from the relay lens (320). In some variations, a 40 diopter or 78 diopter ophthalmic lens may be placed at a distance equal to the focal of length of the objective lens and the focal length of the relay lens. In some variations, the distance between the objective lens (316) and relay lens (320) may be adjusted, which may help to tailor the optical lens assembly to address any refractive errors and/or variability in a patient's eye (e.g., due to anatomical variations in cornea thickness, distance between the anterior chamber and the fundus, corrective lenses such as glasses or contact lenses, etc.) so that a focused image may be acquired by the portable computing device image sensor(s). In some variations, the objective lens may be detachable and/or movable relative to the relay lens. For example, the relay lens (along with one or more of the other components of the optical lens assembly) may be enclosed in a housing comprising an attachment region (350) with a plurality of threaded protrusions (352) and an objective lens mount (600) may comprise a receiving region (654) with a plurality of threaded grooves (602) that correspond with the threaded protrusions (352). Engaging the threaded grooves (602) of the objective lens mount (600) with the threaded protrusions (352) of the optical lens housing (330, 530) may align the center of the objective lens (316) with the center of the relay lens (320), defining a longitudinal axis (360) between the objective lens center and the relay lens center. Turning the objective lens mount may cause the objective lens to travel along the longitudinal axis, changing the distance between the objective lens and the relay lens. A clinician or technician may turn the objective lens mount while inspecting a patient's eye to focus the image/view on the desired region of the eye, compensating for any refractive variations in the patient's eye. Alternatively or additionally, the relay lens may be movable along the longitudinal axis to adjust the image focus. For example, the relay lens may be attached to a slidable mount with a slider mechanism (e.g., manually adjustable or slidable, and/or adjustable or slidable using an actuator or motor). In some variations, the objective lens mount (along with the objective lens attached on the mount) may be de-coupled from the optical lens assembly housing, and exchanged with a different objective lens and mount. A different objective lens and mount may be used for patients with greater refractive variability or fluctuations, and/or for imaging different regions of the eye or different anatomical regions (e.g., wound regions, cervix, or any tissues for which their microstructures are of interest), and/or for replacing a faulty objective lens and mount. Alternatively, in some variations, the distance between the objective lens and the relay lens may be fixed.

Objective Lens Mount

An objective lens mount may retain or secure an objective lens using any suitable retention mechanism. FIGS. 6A and 6B depict one variation of an objective lens mount (300) to which the objective lens (216) may be coupled. The objective lens mount (600) may comprise a groove or slot (601) that has a circular track with a radius and/or diameter that approximates the radius and/or diameter of the objective lens (216). An objective lens mount (600) may comprise a lens release mechanism that allows the objective lens to be removed for repair and/or replacement with a different objective lens with different optical properties (e.g., objective lenses for imaging the anterior portion of the eye instead of the posterior portion of the eye, patients with different eyeglasses prescriptions, etc.). For example, the objective lens mount (600) may comprise two or more shells or frames (604) that may be configured to clamp the objective lens therebetween and secured (e.g., with a latch, elastic band, screw, and/or any other detachable attachment mechanism). In FIGS. 6A and 6B, the objective lens mount (600) comprises first and second frames (604a, 604b) that are symmetric, each contacting half the circumference of the objective lens (216), and having an attachment mechanism (608) for attaching the first and second frames together to retain the objective lens (216) between them. The attachment mechanism (608) may comprise, for example, first and second threaded bores (610a, 610b) on the first and second frames, respectively, and a screw having a corresponding threads and a length that extends through both the first and second threaded bores (also depicted in FIGS. 4A-4C, 5A-5C). Aligning the first and second bores and threading the screw therethrough may secure an objective lens that is clamped between the first and second frames. Alternatively, the objective lens mount may be configured to retain an objective lens permanently, such that the objective lens is not removable from the mount. To use a different objective lens, the entire lens and mount may be removed and replaced with a different objective lens (e.g., having the same or different optical properties) and mount. Alternatively the objective lens may be enclosed in the same housing as the other components of the optical lens assembly (including the relay lens).

While illumination light from multiple light sources may be directed through a beam splitter as described above, in other variations, illumination light from multiple sources may be directed to the illumination optical components through one or more shutters, color wheels, mirrors or reflectors, beam splitters, and/or prisms.

Portable Computing Device Case

A detachable imaging system for generating stereoscopic views of an eye may comprise a portable computing device case. In some variations, the portable computing device case may be integrally formed with the housing of the optical lens assembly, while in other variations, the device case may be detachable from the optical lens assembly. This may allow the device case to be adapted for various portable computing device form factors and/or changes in the housing of portable computing devices, while keeping re-using the optical lens assembly across multiple devices and/or device housing shapes/sizes. A portable computing device case, such as a case for a smartphone, may comprise a frame having one or more attachment mechanisms for coupling the case to the smartphone and a light guide configured to optically connect the light source of the smartphone camera to the optical lens assembly. In one variation, the light guide (or light emitter) may be a fiber optic cable (i.e., optical cable) and the device case may further comprise an optical cable holder or mount with that secures one end of the optical cable (i.e., a first end of the cable) at a location corresponding to the location of the smartphone light source. The cable holder or mount may comprise an enclosure made of an opaque or light-blocking material with an opening that may be, for example, friction-fit over the optical cable. The cable holder or mount may optionally include a flange, lip or other structure that may help further shield the smartphone camera from the smartphone light source. In some variations, a second end of the optical cable may be positioned adjacent to the illumination optical components described above, so that when the smartphone flash is activated, the light from the flash is directed into the patient's eye. Optionally, the optical lens assembly may comprise an illumination light beam splitter and the optical cable may be positioned adjacent to an illumination light beam splitter, which then directs the light into the illumination optical components to the eye. The length of the optical cable between the first end and second end of the cable may be curved, having one or more curves such that light loss along the cable length is reduced and/or the optical cable remains bounded by an area (e.g., back surface area) of the smartphone. Alternatively or additionally, a smartphone case may comprise a white light source that is optically connected to the first end of the cable. The smartphone case may further comprise a communication module that provides electrical communication (wired or wireless, e.g., Bluetooth) between the smartphone and the white light source. When an image is to be acquired, a command is sent from the smartphone to the communication module, which activates the white light source causing a transmission of light through the optical cable and transmits illumination light to the eye. In some variations, the white light source of the smartphone case may have a higher light output than the light source of the smartphone.

Figure 8A:
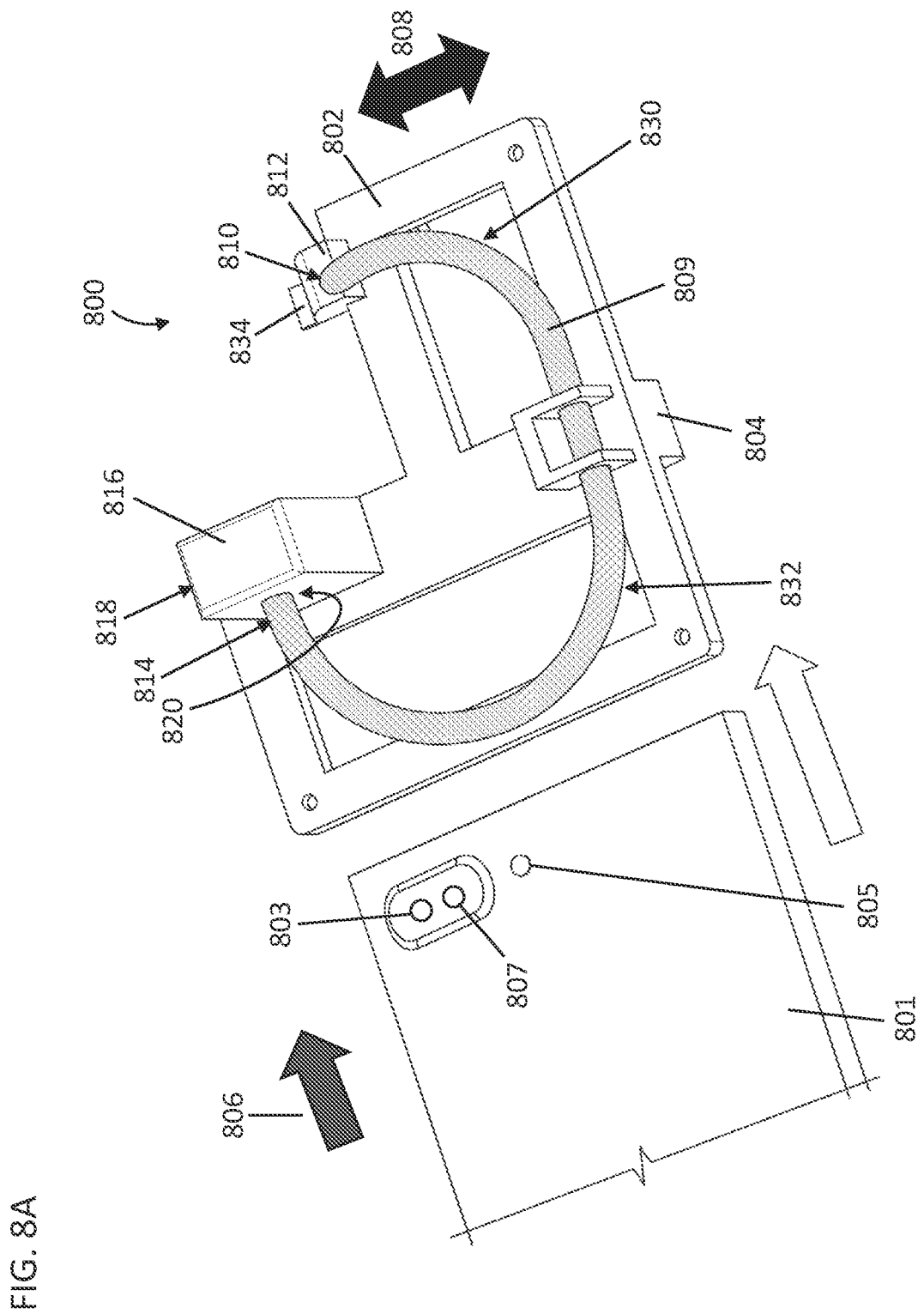
FIG. 8A is an elevated perspective view of one variation of a portable computing device case of an imaging system for acquiring images for generating stereoscopic views of the eye.

One variation of a smartphone case of a detachable imaging system for generating stereoscopic views of an eye is depicted in FIG. 8A (the optical lens assembly is omitted for the sake of clarity). The smartphone (801) may comprise a first and second camera lens (803, 807), as described previously. Optionally, the smartphone may comprise a flash light source (805) adjacent to the camera lenses and/or between the camera lenses. A smartphone case (800) may comprise a frame (802) comprising two or more clips or feet (804) along its perimeter for engaging the perimeter of a smartphone (801). For example, the clips or feet (804) may comprise a protrusion and/or lip that wrap around the edge of the smartphone, having a length that approximates the thickness of the smartphone. In this variation, the smartphone (801) may be slid in the direction of arrow (806) (e.g., vertical direction), as depicted in FIG. 8A into engagement with the smartphone case (800). The clips or feet (804) may allow relative motion between the smartphone and the smartphone case in the vertical direction, but may limit lateral motion (i.e., in a direction represented by arrow (808) which may be perpendicular to the vertical direction). The smartphone case (800) may also comprise a fiber optic cable (809) with a first end (810) coupled to a cable holder or mount (812) and a second end (814) coupled to an optical lens assembly mount (816). The optical lens assembly mount (816) may comprise a slot (818) that corresponds with the size and shape of the portion of the optical lens assembly housing. The optical lens assembly mount (816) may also comprise an opening (820) having a diameter that corresponds with the diameter of the optical cable, and/or an opening or window for a light source.

Figure 8B:
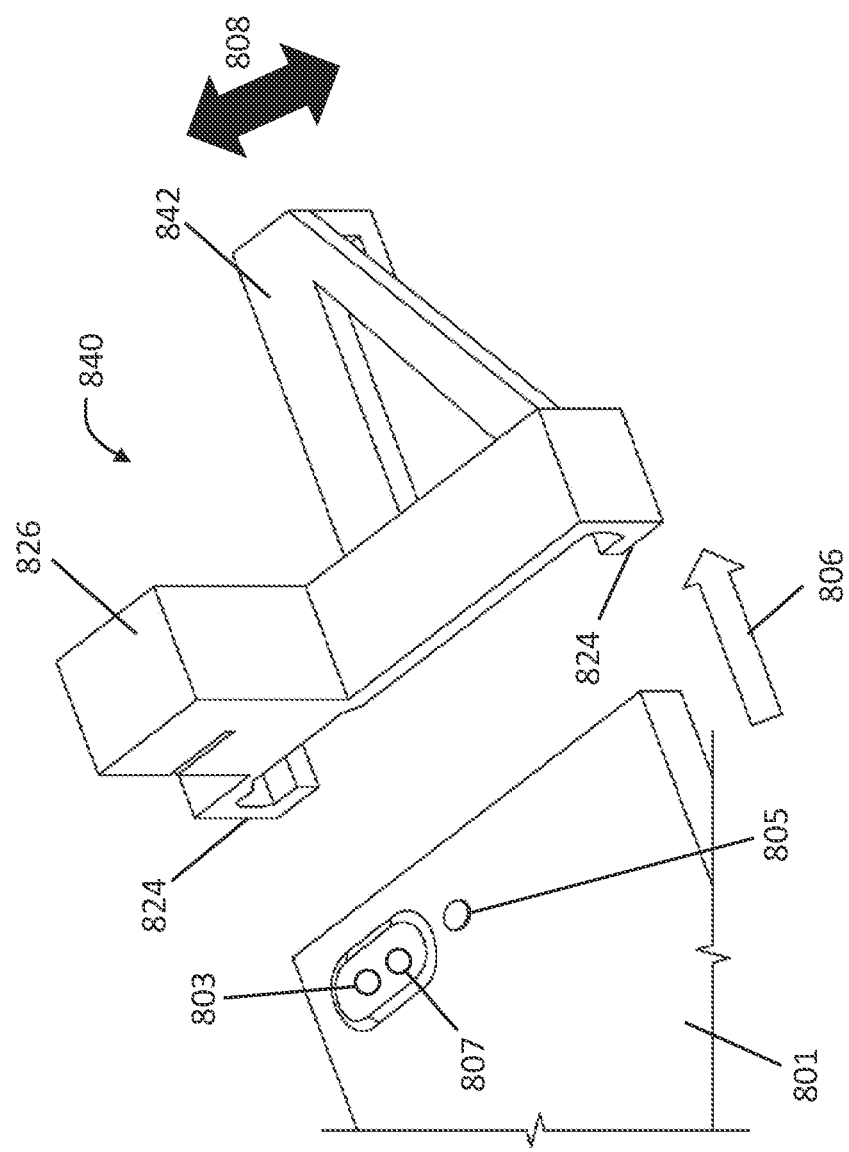
FIG. 8B is an elevated perspective view of another variation of a portable computing device case of an imaging system for acquiring images for generating stereoscopic views of the eye.

FIG. 8B depicts a portable computing device case (840) having a light source (e.g., LED), where an optical cable may not be used to direct light from the light source or portable computing device light source to the optical lens assembly. The light source may be located within the optical lens assembly mount housing (826), and/or may be located outside of the optical lens assembly mount (826), but provide illumination through an opening or window in the housing of the optical lens assembly (e.g., window (331) depicted in FIGS. 3A and 5A) such that illumination is directed through the optical lens assembly and to the patient's eye, as explained previously. In some variations, the light source (e.g., LED) may be located within a light source enclosure of the smartphone case, which may comprise opaque (e.g., light-blocking) walls that limit or block stray light. The light source enclosure may comprise an opening or window that abuts or is otherwise optically connected to the opening or window of the optical lens assembly mount (826), so that light may be directed into the optical lens assembly. The smartphone case (840) may comprise a frame (842) comprising two or more clips or feet (824) along its perimeter and/or lateral sides for engaging the perimeter of a smartphone (801). For example, the clips or feet (824) may comprise a protrusion and/or lip that wrap around the edge of the smartphone, having a length that approximates the thickness of the smartphone. In this variation, the smartphone (801) may be slid in the direction of arrow (806) (e.g., vertical direction), as depicted in FIG. 8B into engagement with the smartphone case (840). The clips or feet (824) may allow relative motion between the smartphone and the smartphone case in the vertical direction, but may limit lateral motion (i.e., in a direction represented by arrow (808), which may be perpendicular to the vertical direction).

The smartphone cases of FIGS. 8A-8B may also comprise a shell made of an opaque material that fits over the frame, enclosing the components mounted on the frame, such as the shell of FIG. 1E. This may help to limit or block any light that may leak from the fiber optic cable (809) and associated mounts to shield the clinician and patient from unwanted illumination.

The power source for the light source may comprise an external battery source of any voltage, for example, a 6-volt battery. Alternatively or additionally, power for the light source may be provided by the smartphone via a circuit board control and application or software interface with the smartphone. In some variations, the power source may comprise a rechargeable battery.

Optical Cable

Some variations of a detachable imaging system for generating stereoscopic views of an eye may comprise a light guide such as one or more fiber optic cables. A fiber optic cable (referred to as an optical cable) may comprise a fiber optic cable where some light emanates from the side walls of the cable, known as evanescent waves. The diameter of an optical cable may be selected to approximate or match the diameter of the smartphone flash light source and/or aperture of the smartphone housing from which the flash light is emitted. For example, the diameter of an optical cable may approximately be greater than or equal to the diameter of the smartphone housing flash light source aperture, and may have a diameter from about 4 mm to about 6 mm (e.g., an inner cable diameter of about 5 mm for a smartphone housing aperture of about 4.5 mm, an inner cable diameter of about 4.5 mm for a smartphone housing aperture of about 4 mm, etc.). This may help to improve the capture efficiency of the light produced by the smartphone for guidance to the optical lens assembly. In some variations, the sidewalls of the optical cable may be coated with an optically opaque and/or reflective coating (e.g., aluminum, silver, etc.), and/or may be enclosed in a sheath to help reduce light leakage along its length. The outer surface or layer of the optical cable may comprise a material that promotes reflection or internal scattering of light within the diameter and length of the cable, with may help reduce light loss along the cable length. Alternatively or additionally, some variations may comprise a group or bundle of fiber optic cables that each have a smaller diameter than the light source (e.g., fiber optic with 0.125 mm) that, when bundled together, cover the light source. Some variations may comprise one or more optical fibers with or without cladding, multimode fiber, a light pipe, and/or a rigid light-transmitting rod.

As described above, the first end of the optical cable may be secured at a location on the smartphone case that corresponds with the location of the smartphone flash and the second end of the optical cable may be secured at the optical lens assembly mount (816). The longitudinal portion of the cable between the first and second ends (810, 814) may be curved such that the cable remains within the boundaries of the case. Alternatively or additionally, a light source may be located within the optical lens assembly mount. The one or more curves of the optical cable (809) may have a bending radius that facilitates continuous and/or uninterrupted light transfer across the length of the cable. In some variations, an optical cable may have a threshold radius of curvature (or a threshold bending radius) where a cable curve or bend that does not exceed the threshold allows the cable to continue to channel light without light loss beyond an acceptable tolerance or efficiency. If the optical cable has a bend that exceeds (i.e., is tighter than, having a radius of curvature that is smaller than) the threshold bending radius or radius of curvature, light loss may exceed the acceptable tolerance and/or may disrupt or truncate the light transmission between the first and second ends of the cable. In some variations, the bending radius may be less than or equal to about ten times the diameter of the cable (e.g., a cable having a diameter of about 5 mm may have a maximum bending radius or radius of curvature of about 50 mm). As depicted in FIG. 8A, the position and orientation of the first end of the optical cable may be secured by a cable holder or mount (812). The cable mount (812) may comprise a cable lumen having a location that corresponds with the location of the smartphone flash light source and an orientation that is approximately perpendicular to the smartphone housing for a length before the lumen curves toward being approximately parallel to the smartphone housing. The curve of the cable mount lumen may position and secure the optical cable (809) such that the face of the first end of the optical cable is aligned with the smartphone flash light source when the smartphone is retained within the case. Aligning the face of a fiber optic cable end along the direction of light from a light source may help to increase the amount of light captured within the cable from the light source. If the end of the fiber optic cable is not generally aligned with the direction of light from the light source, or is at an angle that exceeds a threshold angle from the light direction, light from the light source may not enter the cable. That is, if the end of the fiber optic cable is not aligned with the light source and/or the direction of the light emanating from the light source within a threshold alignment angle, insufficient light may be captured in the cable, and little if any illumination may be provided to the optical lens assembly (e.g., the more parallel the optical cable is to the light source, the higher the percentage of light output from the source will be captured and transmitted via the cable). The curved lumen of the cable mount may help to align the optical cable with the smartphone light source at the first end, and then guide it in a curve that may be approximately parallel to the plane of the smartphone housing. In this variation, the path of the optical fiber may have a first curve (830) and a second curve (832), where the ROC of the first and second curves do not exceed the threshold bending radius beyond which light conduction is lossy and/or interrupted (e.g., less than or equal to about ten times the diameter of the cable, as described above). The second end of the optical cable may pass through a slot or opening of the optical lens assembly mount, for optically coupling to the illumination light beam splitter.

A cable holder or mount (812) may comprise one or more structures to help enclose or shield the light from the smartphone light source, and in particular, shield the light from the smartphone light source from the patient (exposure to white light may interfere with pupil dilation) and/or the smartphone image sensor and/or camera optics. For example, a cable mount may comprise a flap that extends from the walls of the cable mount enclosure (e.g., a light shielding flange (834) of FIG. 8A) that may extend along the surface of a smartphone housing to fill in any gaps or spaces between the housing of the optical lens assembly and the smartphone housing so that light from the smartphone light source does not scatter or leak over to the smartphone image sensor. The additional shielding of the smartphone camera may help to reduce glare and ambient lighting that may be caused by stray light from the smartphone light source. The light shielding flange (834) may be located between the smartphone camera and light source and may act as an additional light barrier between these two components. In some variations where the optical lens assembly housing comprises a groove with an opening having a beveled edge around the circumference of the opening (e.g., as described above and depicted in FIGS. 4C-4D), the flange (834) may be shaped to fit engaged with the beveled edge within the groove, which may help shield the smartphone camera lens and/or image sensor from unwanted ambient light that may degrade the image quality.

Optical Lens Assembly Housing and Portable Computing Device Case Interface

In some variations, the optical lens assembly and the portable computing device case of a detachable imaging system may be mounted on a single substrate and not detachable from each other, but releasably attached to a portable computing device. Alternatively, as described above, the optical lens assembly and portable computing device case of a detachable imaging system may be separate modules (i.e., in separate housings or enclosures) and may comprise one or more attachment mechanisms for engaging and securing to each other and/or a portable computing device. Variations of attachment mechanisms of a detachable device for coupling to a smartphone are schematically depicted in FIGS. 1B, 1D, 7B, and 7C. A portable computing device (108) such as a smartphone may comprise a first camera (103) with an image sensor and a lens over the image sensor, and a second camera (107) with an image sensor and a lens over the image sensor. The portable computing device or smartphone (108) may optionally comprise a (flash) light source. In many smartphones, the surfaces of the camera lenses may protrude from the smartphone housing. Turning to FIGS. 1B and 1D, relative motion between the optical lens assembly (102) and the smartphone case (101) and the smartphone may be reduced or eliminated by attachment mechanisms that secure these items together and limit motion in one or more directions. For example, horizontal motion between the case and the smartphone (represented in FIG. 1B by the arrow (168), as well as arrows (808) in FIGS. 8A-8B) may be limited or eliminated by clips or feet on the side of the case that restrain lateral motion while permitting vertical motion (for the smartphone to slide into the case). Vertical motion of the smartphone (represented by arrow (169) in FIGS. 1B-1C, as well as arrows (806) in FIGS. 8A-8B) relative to the case and optical lens assembly may be limited or eliminated by engagement of the optical lens assembly housing groove (e.g., as depicted in FIG. 7C) with the protruding lens surface (703), which may prevent the smartphone from sliding out of the case. The optical lens assembly housing (112, 122) may be coupled to the case (101) by sliding the optical lens assembly (102) into the optical lens assembly mount (118, 132), which may limit or eliminate relative vertical motion between the optical lens assembly (102) and the case (101) (vertical arrow (169) in FIGS. 1B-1C, as well as arrows (808) in FIGS. 8A-8B). The beveled edge (e.g., edge (346) depicted in FIG. 7B) of the groove or notch of the optical lens assembly housing (112, 122) may engage or encase the raised or protruding smartphone camera lens surface such that the smartphone cannot slide vertically past the notch out of the case unless the optical lens assembly is removed.

Turning to FIG. 7C, the optical lens assembly housing (330) may also comprise a groove (451) with a curved contour (362), which may correspond with the curvature (364) of the optical cable mount (366). Aligning these two contours may help to lock optical lens assembly housing with the case and/or may help to provide additional engagement of the detachable imaging system with the smartphone to prevent movement of the optical lens assembly and to maintain proper imaging alignment with the smartphone camera. That is, sliding the optical lens assembly (330) into engagement with the case (371) locks the detachable imaging system over the dual-camera smartphone (372), so that the smartphone does not disengage horizontally or vertically from any component of the detachable imaging system. Turning to FIG. 7B, the optical lens assembly (330) may also comprise a notch (345) having a beveled edge (346). The notch and beveled edges may engage with the protruded lens surface (703) depicted in FIG. 7C. This engagement may also help secure the detachable imaging system with the smartphone/portable computing device. This may allow single-hand operation of the smartphone for image acquisition. By allowing a hand to remain free may facilitate more precise control of the position and/or stabilization of the smartphone and imaging system on the patient's face to acquire a more high-quality image and may also allow the clinician or technician to interact with the controls (e.g., touch screen) of the smartphone.

While a certain arrangement and relative positioning of various components of the detachable imaging system are depicted and described above, it should be understood that the position of one or more of these components may be modified in order to accommodate design changes and/or variations between different portable computing devices. For example, the optical lens assembly mount may be adjusted so that the optical lens assembly (e.g., the relay lens) is aligned with the portable computing device image sensor. The light source may similarly be re-positioned depending on the position of the optical lens assembly mount. The location, size and shape of the optical cable mount may be adjusted based on the location of the portable computing device light source location, size and shape.

Also described herein are kits comprising any of the imaging systems described herein. In some variations, a kit may comprise a first detachable imaging system comprising a near-infrared light source, and/or a second detachable imaging system comprising a white light source, and/or a third detachable imaging system comprising an ultraviolet light source, and/or a fourth detachable imaging system comprising a green or blue light source. Optionally, a kit may also comprise one or more dyes (e.g., fluorescent dyes such as fluorescein or indocyanine green) for application to the eye that may help facilitate the visualization of certain features of the eye. In one variation, a kit may comprise a first detachable imaging system with a white light source for white light imaging, a second detachable imaging system with a 400-500 nm light source for auto-fluorescence imaging, and a third detachable imaging system with a 200-400 nm light source for imaging of fluorescent dyes. For example, a kit may optionally comprise a fluorescence imaging device comprising an optical lens assembly, an ultraviolet light source that is optically connected to the optical lens assembly, and a control circuit that is electrically connected to the ultraviolet light source and optically connected to the portable computing device image sensor. A kit may optionally comprise an auto-fluorescence imaging device comprising an optical lens assembly, a blue or green light source that is optically connected to the optical lens assembly, and a control circuit that is electrically connected to the blue or green light source and optically connected to the portable computing device image sensor. Kits may optionally comprise one or more pairs of prismatic or stereoscopic glasses or a stereoscope to combine images of different vantage points to form a stereoscopic image.

Methods

A method for generating stereoscopic views or images of a patient's eyes may comprise acquiring images using a detachable imaging system (such as any of the detachable imaging systems described herein) disposed over a first camera and a second camera of a portable imaging device (e.g., a smartphone), generating a first view window on a display of the portable computing device depicting images acquired by the first camera and a second view window on the display depicting images acquired by the second camera, and generating a stereoscopic view by combining the images depicted in the first view window and the second view window. The detachable imaging system may be any of the imaging systems described herein, and may comprise, for example, an objective lens with an objective lens focal length and a relay lens with a relay lens focal length that is aligned with the objective lens along an imaging axis. The first camera of the portable computing device may have a first lens with a first focal length and a second camera of the portable computing device having a second lens with a second focal length that may be greater than or equal to the first focal length. The relay lens focal length may be greater than the first focal length and less than or equal to the difference between the second focal length and the objective lens focal length, or may be less than or equal to the second focal length. In the context of generating a stereoscopic view of the fundus or retina of an eye, the pupil may be fully or partially dilated. In the case of full dilation (e.g., about 6 mm or more), an image of a fundus region may be acquired by cameras of the smartphone in a single field-of-view. In the case of insufficient or partial dilation (e.g., less than about 6 mm), the field-of-view may be relatively narrower, and a series of images may be acquired in sequence, where the camera is tilted and/or translated laterally to acquire different portions of the fundus region. These partial images with narrower fields-of-view may be composited together by a controller (e.g., of the portable computing device or a remote controller) in post-processing to simulate a view that may be acquired in full dilation. As described previously, in addition to imaging the eye, the devices and methods described herein may be used to image different anatomic structures (e.g., wound regions, cervix, or any tissues for which their microstructures are of interest).

The first and second view windows may be adjacent to each other on a display of the portable computing device. In some variations, the image data from the cameras may be transmitted to a remote computing device or server and displayed on a remote display device. A stereoscopic view may be obtained by using a pair of prismatic glasses or a stereoscope such that the images in the first view window and the images in the second view window may be viewed simultaneously. Alternatively or additionally, the images from the first camera and the second camera may be overlaid or otherwise composited together. FIG. 9A depicts one variation of a graphical user interface of an application that may be executed on a portable computing device such as a smartphone (900), where the smartphone (900) has a first camera with a wide-field lens (e.g., having a focal length of about 28 mm) and a second camera with a telephoto lens (e.g., having a focal length of about 56 mm). As depicted there, the image or view (902) from the first camera may be displayed in a first window that occupies the majority of the area of the smartphone display, while the image or view (904) from the second camera may be displayed in a second window that is substantially smaller than the first window and/or offset to a side region and/or corner region of the smartphone display. FIG. 9B depicts another variation of a graphical user interface of an application where the image or view (902) from the first camera may be displayed in a first window, and the image or view (904) from the second camera may be displayed in a second window, where both images or views (902, 904) occupy similar areas of the smartphone display. With the use of prismatic glasses or a stereoscope that merges these view windows, an user may obtain a stereoscopic view of the eye. For example, rotating the smartphone (900) into a horizontal or landscape position, as shown in FIG. 9C, may allow for an enlarged stereoscopic view of the eye. Alternatively or additionally, the images acquired by the first and second cameras may be transmitted to a remote computing device or server, which may control a display device or monitor that may be larger than the display of a smartphone. One example of a display device (e.g., a monitor of a desktop computer) is depicted in FIG. 9D. This display device (908) may provide a more immersive stereoscopic experience, and may facilitate examination of the eye by a remote clinician. The images on the display device (908) may be dynamically updated (e.g., in real-time). In some variations, the images acquired by the cameras on the portable computing device may be processed by a remote computing device or server to generate a virtual reality (VR) or augmented reality (AR) environment that may be transmitted to a VR headset or AR headset. The images may be updated in real-time, and may provide a stereoscopic view and/or VR or AR environment for a remote user. For example, a clinician may acquire images of a patient's eye in a medical office, transmit those images to a remote computing device or server that generates a stereoscopic view and/or VR or AR environment for an eye care specialist (e.g., an ophthalmologist), who may be able to view the patient's eye in real-time and provide a diagnosis and/or other advice.

In situations where the eye is not sufficiently or fully dilated (e.g., pupil dilation is less than about 6 mm), the field-of-view of one of the two cameras may be limited to a smaller region of the fundus. In order to capture images of a larger fundus region, the smartphone may be laterally translated to capture two portions of the fundus region which may then be combined or stitched together to simulate a larger view. FIG. 9E schematically depicts a first set of views when the smartphone (900) is at a first location and FIG. 9F schematically depicts a second set of views when the smartphone (900) is at a second location that is a lateral translation from the first location. The first and second sets of views from FIGS. 9E to 9F may be combined and displayed in view windows similar to that depicted in FIG. 9C.

When a particular image view and/or light data and/or image data is to be saved, the user may trigger the smartphone (900) to acquire the image by, for example, pressing a button (910), key, and/or graphic (912) on a touch-sensitive screen of the portable computing device.

Although particular embodiments or variations of the present inventions have been shown and described, it will be understood that it is not intended to limit the present inventions to the disclosed embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

The invention claimed is:

1. A detachable imaging device configured to provide stereoscopic views for a portable computing device having two cameras, the imaging device comprising:
   a portable computing device case configured to be detachably coupled to a portable computing device that comprises a first camera having a first lens with a first focal length, and a second camera having a second lens having a second focal length longer than the first focal length, wherein the position of the first and second cameras are fixed relative to each other and the first and second lenses are coplanar; and
   an optical lens assembly detachably coupled to the portable computing device case, the optical lens assembly comprising an objective lens with an objective lens focal length and a relay lens with a relay lens focal length, wherein the relay lens focal length is less than or equal to the second focal length and greater than the first focal length.

2. The imaging device of claim 1, wherein the relay lens focal length is less than or equal to the difference between the second focal length and the objective lens focal length and greater than the first focal length.

3. The imaging device of claim 1, wherein a center of the objective lens and a center of the relay lens are aligned along an imaging axis, and a distance between the objective lens and the relay lens is a sum of the objective lens focal length and the relay lens focal length.

4. The imaging device of claim 1, wherein the optical lens assembly is configured to be disposed over the first and second cameras when the imaging device is coupled to the portable computing device.

5. The imaging device of claim 1, wherein the portable computing device case comprises a light emitter.

6. The imaging device of claim 5, wherein the light emitter comprises a fiber optic cable that optically connects the optical lens assembly with a light source of the portable computing device.

7. The imaging device of claim 5, wherein the light emitter comprises a light source.

8. The imaging device of claim 7, wherein the light source comprises a light-emitting diode.

9. The imaging device of claim 1, wherein the first focal length is about 28 mm, the second focal length is about 56 mm, the objective lens focal length is about 18.5 mm, and the relay lens focal length is about 30 mm.

10. The imaging device of claim 1, wherein the objective lens focal length is about 25 mm.

11. The imaging device of claim 1, wherein the objective lens is detachably coupled to an optical lens assembly housing of the optical lens assembly.

12. The imaging device of claim 11, wherein the objective lens is retained within an objective lens mount, and wherein the optical lens assembly housing comprises an attachment region with a plurality of threaded protrusions, and the objective lens mount comprises a receiving region with a plurality of threaded grooves that correspond with the threaded protrusions.

13. The imaging device of claim 1, wherein a diameter of the relay lens is greater than or equal to the sum of a diameter of the first lens, a diameter of the second lens, and a separation distance between the first and second cameras.

14. An imaging system for generating stereoscopic views, the system comprising:
   a portable computing device comprising a first camera having a first lens with a first focal length, and a second camera having a second lens with a second focal length that is greater than or equal to the first focal length, wherein the first and the second cameras are adjacent to each other and the first and second lenses are coplanar; and
   a detachable imaging system comprising a portable computing device case configured to releasably attach to the portable computing device and an optical lens assembly configured to be disposed over the first and second camera when the detachable imaging system is coupled to the portable computing device, wherein the portable computing device case has a light emitter mounted thereon that is optically connected to the optical lens assembly, and wherein the optical lens assembly has an objective lens with an objective lens focal length and a relay lens with a relay lens focal length, and wherein the relay lens focal length is less than or equal to the second focal length and greater than the first focal length.

15. The system of claim 14, wherein the relay lens focal length is less than or equal to the difference between the second focal length and the objective lens focal length and greater than the first focal length.

16. The system of claim 14, wherein the portable computing device comprises a light source and the light emitter comprises a fiber optic cable.

17. The system of claim 14, wherein the light emitter comprises a light source.

18. The system of claim 17, wherein the light source comprises a light-emitting diode.

19. The system of claim 14, wherein a center of the objective lens and a center of the relay lens are aligned along an imaging axis, and a distance between the objective lens and the relay lens is a sum of the objective lens focal length and the relay lens focal length.

20. The system of claim 19, wherein the imaging axis intersects at a midpoint of a separation distance between the first and second cameras.

21. The system of claim 14, wherein a central axis of the first camera and a central axis of the second camera are parallel, and a separation distance between the first and second cameras is less than or equal to about 30 mm.

22. The system of claim 21, wherein illumination light from the optical lens assembly has an illumination axis that is offset from the central axes of the first and second cameras.

23. The system of claim 21, wherein the separation distance and orientations of the first and second lenses are fixed.

24. The system of claim 14, wherein the first lens is a wide-angle lens and the second lens is a telephoto lens.

25. The system of claim 14, wherein the first focal length is about 28 mm, the second focal length is about 56 mm, the objective lens focal length is about 18.5 mm, and the relay lens focal length is about 30 mm.

26. The system of claim 14, wherein the portable computing device is a smartphone.

27. The system of claim 14, wherein the optical lens assembly is releasably attached to the portable computing device case.

28. The system of claim 14, wherein a diameter of the relay lens is greater than or equal to the sum of a diameter of the first lens, a diameter of the second lens, and a separation distance between the first and second cameras.

29. A method for generating stereoscopic views using a dual-camera portable computing device, the method comprising:

simultaneously acquiring images using a detachable imaging system disposed over a first camera and a second camera of a portable computing device, wherein the detachable imaging system comprises an objective lens with an objective lens focal length and a relay lens with a relay lens focal length and is aligned with the objective lens along an imaging axis, wherein the first camera of the portable computing device having a first lens with a first focal length and a second camera of the portable computing device having a second lens with a second focal length that is longer than the first focal length, and wherein the relay lens focal length is less than or equal to the second focal length and greater than the first focal length;

generating a first view window on a display of the portable computing device depicting images acquired by the first camera and a second view window on the display depicting images acquired by the second camera; and generating a stereoscopic view by combining the images depicted in the first view window and the second view window.

30. The method of claim 29, wherein the relay lens focal length is less than or equal to the difference between the second focal length and the objective lens focal length and greater than the first focal length.

31. The method of claim 29, wherein a diameter of the relay lens is greater than or equal to the sum of a diameter of the first lens, a diameter of the second lens, and a separation distance between the first and second cameras.

32. The method of claim 29, wherein combining the images comprises viewing the images in the first view window and the second view window using a pair of prismatic or stereoscopic glasses, or a stereoscope.

33. The method of claim 29, wherein combining the images comprises overlaying the images from the first camera and the second camera.

* * * * *